(12) United States Patent
Jamal et al.

(10) Patent No.: US 12,350,446 B2
(45) Date of Patent: Jul. 8, 2025

(54) METHOD OF USING A STABILIZER FOR A DELIVERY SYSTEM

(71) Applicant: Edwards Lifesciences Corporation, Irvine, CA (US)

(72) Inventors: Deena Walid Jamal, San Ramon, CA (US); Hieu Minh Luong, Westminster, CA (US); Garrett Dallas Johnson, Costa Mesa, CA (US); Tarannum Ishaq Gutierrez, Ladera Ranch, CA (US); Matthew Michael Becerra, Lake Forest, CA (US); Karen Fromell Nesbitt, Newport Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 73 days.

(21) Appl. No.: 18/083,404

(22) Filed: Dec. 16, 2022

(65) Prior Publication Data

US 2023/0118545 A1 Apr. 20, 2023

Related U.S. Application Data

(63) Continuation of application No. 18/073,760, filed on Dec. 2, 2022, now Pat. No. 12,109,371, which is a
(Continued)

(51) Int. Cl.
| | |
|---|---|
| *A61F 2/24* | (2006.01) |
| *A61B 90/10* | (2016.01) |
| *A61B 90/57* | (2016.01) |
| *A61M 25/01* | (2006.01) |
| *A61M 25/00* | (2006.01) |

(52) U.S. Cl.
CPC ....... *A61M 25/0113* (2013.01); *A61F 2/2427* (2013.01); *A61M 25/0097* (2013.01); *A61M 25/0136* (2013.01); *A61M 2205/0272* (2013.01); *A61M 2209/01* (2013.01)

(58) Field of Classification Search
CPC .......... A61M 25/0113; A61M 25/0097; A61M 25/0136; A61M 2209/01; A61F 2/95–97; A61F 2/2427–2439; A61B 90/10; A61B 90/11; A61B 90/50; A61B 34/30–34/37; A61B 90/57
See application file for complete search history.

(56) References Cited

U.S. PATENT DOCUMENTS

| | | |
|---|---|---|
| 2,876,359 A | 3/1959 | Langley |
| 4,001,556 A | 1/1977 | Folchi et al. |

(Continued)

FOREIGN PATENT DOCUMENTS

| | | |
|---|---|---|
| DE | 102013002813 A1 | 8/2014 |
| EP | 2603273 A1 | 6/2013 |

(Continued)

*Primary Examiner* — Kathleen S Holwerda
(74) *Attorney, Agent, or Firm* — Thomas C. Richardson

(57) ABSTRACT

Disclosed herein are embodiments of methods of using stabilizers for use in delivering a replacement heart valve. The stabilizers can receive a portion of a delivery system, such as a handle, to prevent unwanted motion of the delivery system. The stabilizer can include a linear actuator for adjusting a position of the delivery system once held within the stabilizer.

20 Claims, 31 Drawing Sheets

Related U.S. Application Data continuation of application No. 16/582,307, filed on Sep. 25, 2019, now Pat. No. 11,931,525.

(60) Provisional application No. 62/741,416, filed on Oct. 4, 2018.

(56) References Cited

U.S. PATENT DOCUMENTS

| | | |
|---|---|---|
| 4,365,488 A | 12/1982 | Mochida et al. |
| 4,585,443 A | 4/1986 | Kaufman |
| 4,617,916 A | 10/1986 | LeVahn et al. |
| 4,686,997 A | 8/1987 | Oloff et al. |
| 5,097,827 A * | 3/1992 | Izumi .................. A61M 25/02 |
| | | 128/911 |
| 5,098,048 A | 3/1992 | Chen |
| 5,184,601 A | 2/1993 | Putman |
| 5,314,411 A | 5/1994 | Bierman et al. |
| 5,405,110 A | 4/1995 | Mistretta |
| 5,413,120 A | 5/1995 | Grant |
| 5,571,072 A | 11/1996 | Kronner |
| 5,586,163 A | 12/1996 | Goldstein |
| 5,876,325 A | 3/1999 | Mizuno et al. |
| 6,332,874 B1 | 12/2001 | Eliasen et al. |
| 7,018,362 B2 | 3/2006 | Bierman et al. |
| 7,220,246 B2 | 5/2007 | Raulerson et al. |
| 7,776,017 B2 | 8/2010 | Ponzi et al. |
| 7,950,306 B2 | 5/2011 | Stuart |
| 8,162,898 B1 | 4/2012 | Wright |
| 8,211,064 B2 | 7/2012 | Sloan |
| 8,277,420 B2 | 10/2012 | Bierman et al. |
| 8,608,705 B2 | 12/2013 | Peters et al. |
| 8,708,952 B2 | 4/2014 | Cohen et al. |
| 8,734,400 B2 | 5/2014 | Ciccone |
| 8,808,248 B2 | 8/2014 | Schultz |
| 8,827,960 B2 | 9/2014 | Haak |
| 9,056,187 B2 | 6/2015 | Rosenberg et al. |
| 9,163,893 B1 | 10/2015 | Gutierrez |
| 9,247,866 B2 | 2/2016 | Aferzon |
| 9,278,193 B2 | 3/2016 | Haider et al. |
| 9,398,922 B2 | 7/2016 | Parihar et al. |
| 9,433,754 B2 | 9/2016 | Mogg |
| 9,480,822 B2 | 11/2016 | Kaiser |
| 2002/0049498 A1 | 4/2002 | Yuksel et al. |
| 2002/0177789 A1 | 11/2002 | Ferry et al. |
| 2003/0081953 A1 | 5/2003 | Wei |
| 2005/0234293 A1* | 10/2005 | Yamamoto ............ A61B 90/57 |
| | | 600/102 |
| 2005/0234435 A1 | 10/2005 | Layer |
| 2006/0058738 A1 | 3/2006 | Ponzi et al. |
| 2006/0241745 A1 | 10/2006 | Solem |
| 2007/0055289 A1 | 3/2007 | Scouten et al. |
| 2007/0149955 A1 | 6/2007 | Edoga et al. |
| 2008/0188869 A1 | 8/2008 | Weitzner et al. |
| 2008/0306442 A1 | 12/2008 | Bardsley et al. |
| 2009/0216197 A1 | 8/2009 | Russo |
| 2009/0247942 A1 | 10/2009 | Kirschenman |
| 2009/0270677 A1 | 10/2009 | Dillon |
| 2009/0319037 A1 | 12/2009 | Rowe et al. |
| 2010/0010449 A1 | 1/2010 | Leibowitz et al. |
| 2010/0010475 A1 | 1/2010 | Teirstein et al. |
| 2010/0117281 A1 | 5/2010 | Doyle |
| 2010/0286478 A1 | 11/2010 | Ewers et al. |
| 2011/0001022 A1 | 1/2011 | Edinger |
| 2011/0015490 A1 | 1/2011 | Trovato et al. |
| 2011/0130718 A1 | 6/2011 | Kidd et al. |
| 2011/0152609 A1 | 6/2011 | Trusty et al. |
| 2011/0152779 A1 | 6/2011 | Panotopoulos |
| 2012/0004502 A1 | 1/2012 | Weitzner et al. |
| 2012/0016312 A1 | 1/2012 | Brown et al. |
| 2012/0065464 A1 | 3/2012 | Ellis et al. |
| 2012/0069965 A1 | 3/2012 | Scheffer et al. |
| 2012/0078355 A1 | 3/2012 | Zipory et al. |
| 2012/0330411 A1 | 12/2012 | Gross et al. |
| 2013/0066342 A1 | 3/2013 | Dell et al. |
| 2014/0142695 A1 | 5/2014 | Gross et al. |
| 2014/0207231 A1 | 7/2014 | Hacohen et al. |
| 2014/0243963 A1 | 8/2014 | Sheps et al. |
| 2014/0249546 A1 | 9/2014 | Shvartsberg et al. |
| 2015/0005733 A1 | 1/2015 | Le et al. |
| 2015/0112427 A1 | 4/2015 | Schweich, Jr. et al. |
| 2015/0133958 A1 | 5/2015 | Singh et al. |
| 2015/0142100 A1 | 5/2015 | Morriss et al. |
| 2015/0190201 A1 | 7/2015 | Olson |
| 2015/0272734 A1 | 10/2015 | Sheps et al. |
| 2016/0249991 A1 | 9/2016 | Glozman et al. |
| 2017/0007101 A1 | 1/2017 | Dejima |
| 2017/0042678 A1* | 2/2017 | Ganesan ................ A61F 2/2439 |
| 2017/0100201 A1* | 4/2017 | Ho ........................ A61B 90/11 |
| 2017/0246435 A1 | 8/2017 | Oveland |
| 2017/0265894 A1 | 9/2017 | Mark et al. |
| 2018/0344457 A1 | 12/2018 | Gross et al. |
| 2020/0230352 A1 | 7/2020 | McNiven et al. |

FOREIGN PATENT DOCUMENTS

| | | |
|---|---|---|
| KR | 10-0977615 B1 | 8/2010 |
| WO | 03082121 A2 | 10/2003 |
| WO | 2017143204 A1 | 8/2017 |

* cited by examiner

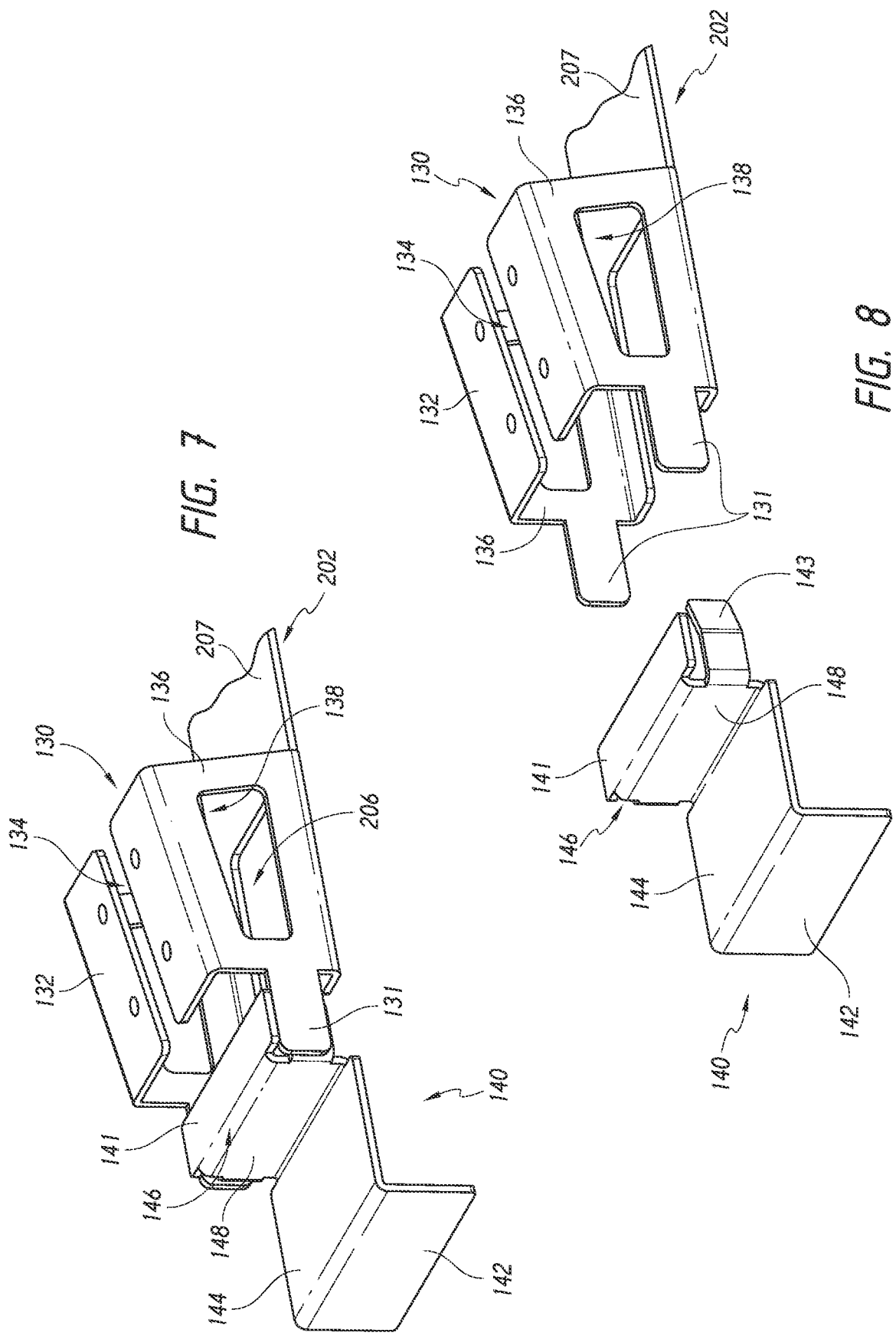

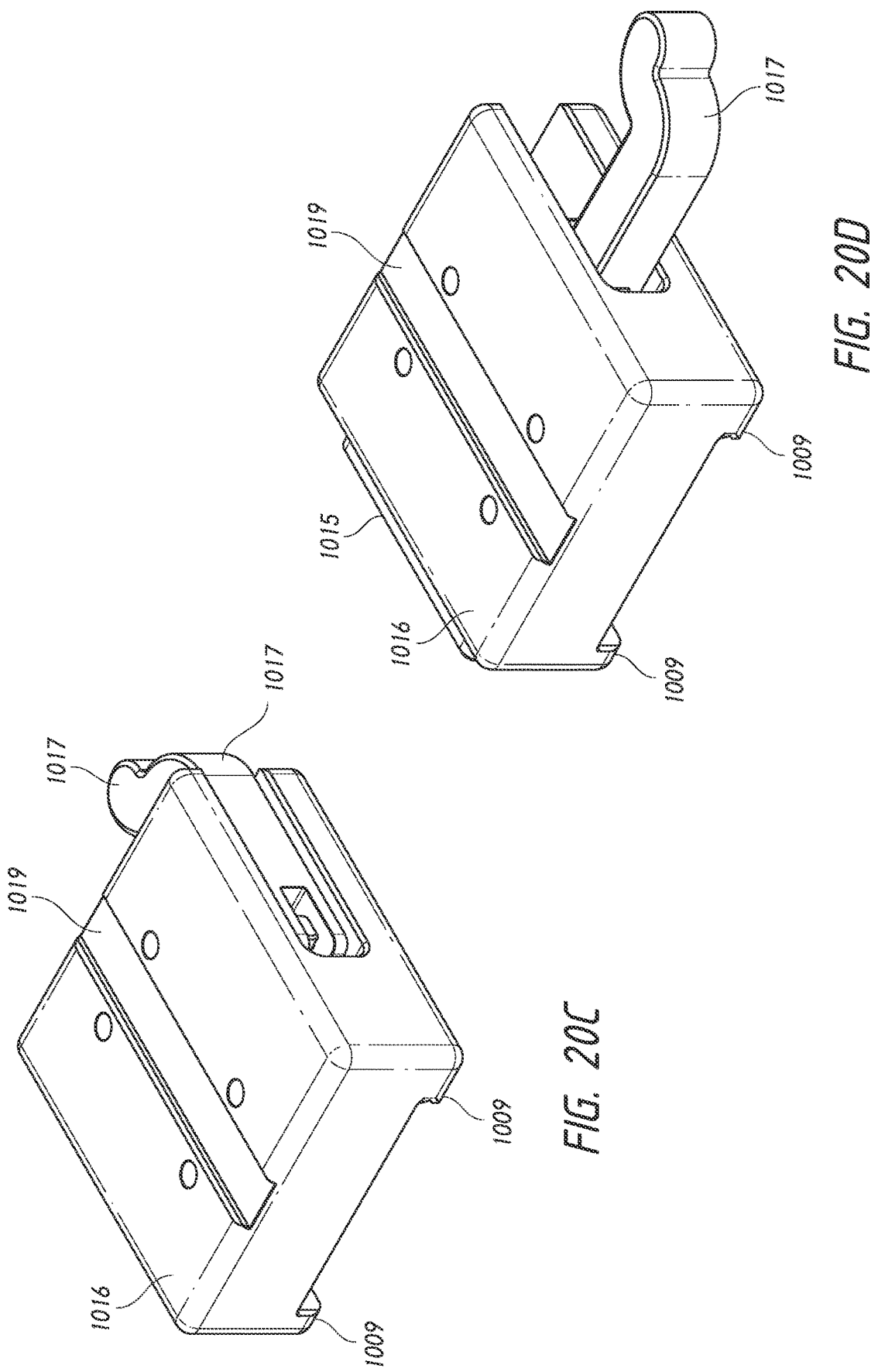

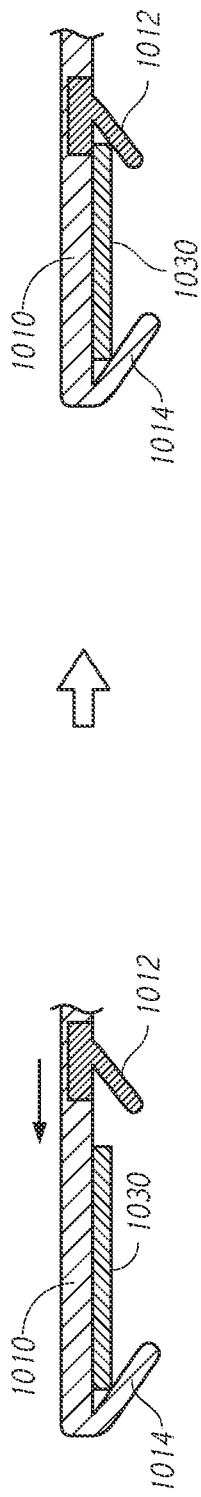
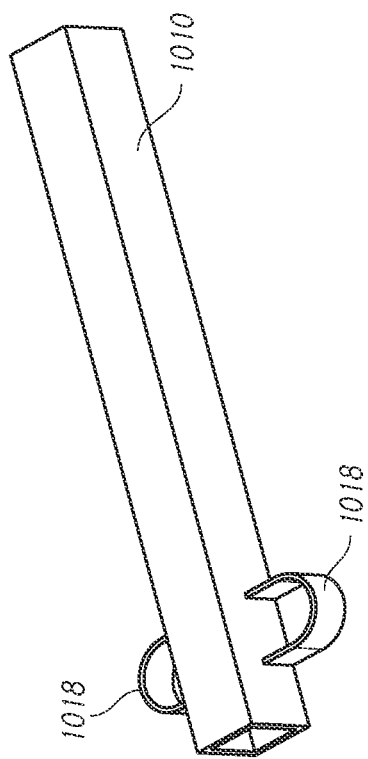

METHOD OF USING A STABILIZER FOR A DELIVERY SYSTEM

PRIORITY CLAIM AND INCORPORATION BY REFERENCE TO ANY PRIORITY APPLICATIONS

This application is a continuation of U.S. application Ser. No. 18/073,760, filed Dec. 2, 2022, which is a continuation of U.S. application Ser. No. 16/582,307, filed Sep. 25, 2019, which claims the benefit of U.S. Provisional Application No. 62/741,416, filed Oct. 4, 2018, entitled "STABILIZER FOR A DELIVERY SYSTEM", the entireties of each of which are hereby incorporated by reference.

BACKGROUND

Field

Certain embodiments disclosed herein relate generally to delivery systems for a prosthesis, and in some embodiments relate to a stabilizer for use with a delivery system for delivering a replacement heart valve through a transseptal approach.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life-threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the location of a delivery system and the deployment of the prosthesis at the desired location can also be challenging.

SUMMARY

The present disclosure includes, but is not limited to, the following embodiments.

Embodiment 1: A stabilizer for a delivery system. The stabilizer can comprise an elongated main body. The elongated main body can comprise a proximal end and a distal end and a longitudinal axis extending between the proximal end and the distal end. The elongated main body can comprise a generally flat base plate extending between the proximal and the distal end. The elongated main body can comprise a first angled surface. The first angled surface can be located on top of the base plate. The first angled surface can be sloped downwardly toward the distal end. The elongated main body can comprise a second angled surface. The second angled surface can be located on top of the base plate. The second angled surface can be spaced longitudinally away from and proximal of the first angled surface. The second angled surface can be sloped downwardly toward the distal end. The stabilizer can further include a hub nest. The hub nest can be attachable on top of the first angled surface. The hub nest can comprise an extension extending upwards from the first angled surface. The extension can be configured to releasably hold a sheath hub of the delivery system. The stabilizer can further include a handle carriage. The handle carriage can be on top of the second angled surface. The handle carriage can comprise a track attachable to the second angled surface and a delivery system clamp configured to longitudinally travel along the track. The delivery system clamp can be configured to releasably hold a handle of the delivery system. The stabilizer can further include a base adapter, wherein the distal end of the main body is configured to releasably connect with the base adapter.

Embodiment 2: The stabilizer of Embodiment 1, further comprising a pair of attachment claims, wherein each of the pair of attachment clamps does not have any sharp ends.

Embodiment 3: The stabilizer of Embodiment 1 or Embodiment 2, wherein the base adapter comprises a pair of proximally extending arms and an upper tab configured to receive distally extending tabs of the main body to prevent upward motion of the main body.

Embodiment 4: The stabilizer of any one of Embodiments 1-3, wherein the first angled surface and the second angled surface are configured to be individually angularly adjusted with respect to the flat base plate.

Embodiment 5: The stabilizer of any one of Embodiments 1-4, wherein the handle carriage comprises a first knob configured to longitudinally translate the delivery system clamp along the housing and a second knob configured to open and close the delivery system clamp.

Embodiment 6: The stabilizer of any one of Embodiments 1-5, further comprising a travel screw located within the housing, wherein a portion of the delivery system clamp is located within the housing and interfaces with the travel screw.

Embodiment 7: The stabilizer of any one of Embodiments 1-6, wherein the first angled surface has a lower height relative to the base plate than the second angled surface.

Embodiment 8: The stabilizer of any one of Embodiments 1-6, wherein the first angled surface has approximately the same angle on a top surface of the first angled surface as a top surface on the second angled surface.

Embodiment 9: The stabilizer of any one of Embodiments 1-8, wherein the first angled surface and the second angled surface each have an angle between 5 and 30 degrees.

Embodiment 10: The stabilizer of any one of Embodiments 1-9, wherein the extension comprises a pair of arms.

Embodiment 11: The stabilizer of Embodiment 10, wherein the pair of arms comprises a spring plunger configured to hold the sheath hub.

Embodiment 12: The stabilizer of Embodiments 1-11, wherein a motor is configured to translate the delivery system clamp along the track, and wherein the motor is configured to open and close the delivery system clamp.

Embodiment 13: The stabilizer of Embodiment 12, wherein the motor is configured to be operated remotely.

Embodiment 14: A stabilizer system comprising the stabilizer of any one of Embodiments 1-13, and further comprising a pair of attachment clamps configured to attach the main body to a base, a first of the pair of attachment clamps attachable to the base adapter and a second of the pair of attachment clamps attachable to the main body.

Embodiment 15: A stabilizer system comprising the stabilizer of any one of Embodiments 1-13, and further comprising a delivery system.

Embodiment 16: The stabilizer system of Embodiment 15, wherein the delivery system comprises a handle, wherein a portion of the delivery system distal to the handle is releasably held within the hub nest and the handle is releasably held within the delivery system clamp of the handle carriage.

Embodiment 17: The stabilizer system of Embodiment 15 or Embodiment 16, wherein the delivery system is configured for transseptal delivery of a replacement mitral heart valve.

Embodiment 18: A stabilizer system comprising the stabilizer of any one of Embodiments 1-17, and further comprising a base having a generally flat upper surface and a plurality of legs extending downwards.

Embodiment 19: The stabilizer system of Embodiment 18, wherein the stabilizer is configured to clamp onto the generally flat upper surface of the base.

Embodiment 20: The stabilizer system of Embodiment 18 or Embodiment 19, and further comprising a generally flat plate, wherein the plurality of legs are configured to be located on the generally flat plate.

Embodiment 21: The stabilizer system of any one of Embodiments 18-20, wherein the stabilizer is configured to magnetically attach to the generally flat upper surface of the base.

Embodiment 22: The stabilizer system of Embodiment 21, wherein the magnetically attachment comprises electromagnetically attachment.

Embodiment 23: A stabilizer for a delivery system. The stabilizer can comprise a main body comprising a proximal end, a distal end and a longitudinal axis extending between the proximal end and the distal end. The stabilizer can comprise a handle carriage. The handle carriage can be provided at a proximal location along the main body. The handle carriage can comprise an angled track that is sloped downwardly toward the distal end of the main body. The handle carriage can comprise a delivery system clamp configured to longitudinally travel along the track. The delivery system clamp can be configured to releasably hold a handle of the delivery system. The stabilizer can include a nest. The nest can be positioned at a distal location along the main body. The nest can be configured to releasably hold a portion of the delivery system.

Embodiment 24: The stabilizer of Embodiment 23, wherein the main body comprises a first angled surface configured to support the nest and a second angled surface proximal to the first angled surface configured to support the handle carriage.

Embodiment 25: The stabilizer of Embodiment 23 or Embodiment 24, further comprising a base adapter releasably attachable to the main body.

Embodiment 26: A method of using the stabilizer of any of the preceding Embodiments to control a delivery system.

Embodiment 27: A universal stabilizer for a delivery system, the universal stabilizer comprising a longitudinally extending rail having an upper facing surface and a lower facing surface, a stationary clamp attached to the lower facing surface of the longitudinally extending rail, a moveable clamp attached to the lower facing surface of the longitudinally extending rail and spaced longitudinally away from the stationary clamp, wherein the moveable clamp is configured to translate along the longitudinally extending rail, and a rail dock attached to the upper facing surface of the longitudinally extending rail, the rail dock configured to mate with a delivery system holder on an upper facing surface of the rail dock, wherein the rail dock is configured to translate along the longitudinally extending rail.

Embodiment 28: The universal stabilizer of Embodiment 27, wherein the rail is a picatinny rail.

Embodiment 29: The universal stabilizer of Embodiment 27 or 28, wherein the moveable clamp comprises a knob configured to adjust a longitudinal position of the moveable clamp.

Embodiment 30: The universal stabilizer of any one of Embodiments 27-29, wherein the rail dock comprises a handle connected to a plate on an opposite side of the rail dock, wherein activation of the handle prevents the rail dock from translating on the longitudinally extending rail.

Embodiment 31: The universal stabilizer of any one of Embodiments 27-30, wherein the delivery system holder comprises a handle carriage comprising a track and a delivery system clamp configured to longitudinally travel along the track, wherein the delivery system clamp is configured to releasably hold a handle of a delivery system.

Embodiment 32: The universal stabilizer of any one of Embodiments 27-31, wherein the longitudinally extending rail further comprises a first pair of outwardly extending protrusions forming a first cavity between and a second pair of outwardly extending protrusions forming a second cavity between, the first pair of outwardly extending protrusions being on an opposite side of the rail from the second pair of outwardly extending protrusions.

Embodiment 33: The universal stabilizer of any one of Embodiments 27-32, further comprising a second rail dock attached to the upper facing surface of the longitudinally extending rail and spaced apart from the rail dock, the second the rail dock configured to mate with a second delivery system holder on an upper facing surface of the second rail dock, wherein the second rail dock is configured to translate along the longitudinally extending rail.

Embodiment 34: A motorized control stabilizer system for a delivery device having a handle with plurality of actuators, the system comprising a knob control system configured to individually operate each of the plurality of actuators, the knob control system comprising a container configured to at least partially encompass the handle, a plurality of stationary sections located within the container and configured to hold the handle in a position, a plurality of roller sections located within the container, each of the plurality of roller sections containing at least one roller, and a motor configured to operate the at least one roller in each of the plurality of roller sections individually, wherein the at least one roller in each of the plurality of roller sections is configured to operate an actuator of the plurality of actuators when the at least one roller is operated, and a handle control system configured to translate the handle of the delivery device, the handle control system comprising a band configured to at least partially surround the container and rotate the container and handle upon translation of the band, a stand connected to the band, and a track in communication with the stand, wherein the stand is configured to translate along the track.

Embodiment 35: The motorized control stabilizer system of Embodiment 34, further comprising a controller to electronically operate the motorized control stabilizer system.

Embodiment 36: The motorized control stabilizer system of Embodiment 34 or 35, wherein the container comprises a distal aperture, and wherein shafts extending from the handle of the delivery device are configured to extend through the distal aperture.

BRIEF DESCRIPTION OF THE DRAWINGS

FIGS. 7-8 illustrate embodiments of a distal end of the stabilizer main body and a base adapter.

FIGS. 20A-20F illustrate embodiments of a rail dock.

FIGS. 26A-26B illustrate embodiments of a moveable clamp attaching to a surface.

FIG. 27 illustrates an embodiment of a rail having wings.

DETAILED DESCRIPTION

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic, tricuspid, or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral (or transseptal) delivery approach, it should be understood that these embodiments can be used for other delivery approaches such as, for example, transapical or transjugular approaches. Moreover, it should be understood that certain of the features described in connection with some embodiments can be incorporated with other embodiments, including those which are described in connection with different delivery approaches.

Stabilizer

Figure 1A:
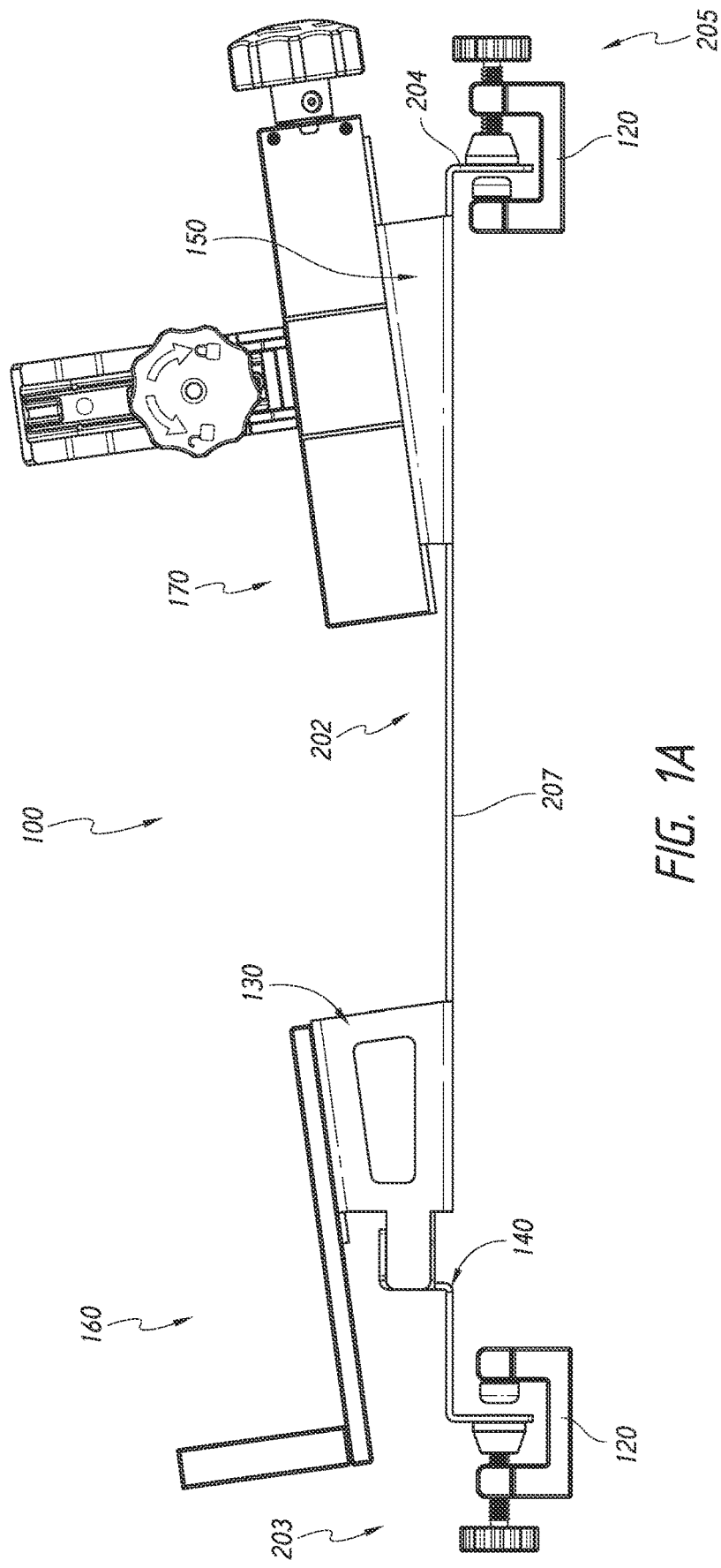
FIGS. 1A-1B illustrate an embodiment of a stabilizer for a delivery system.
Figure 1B:
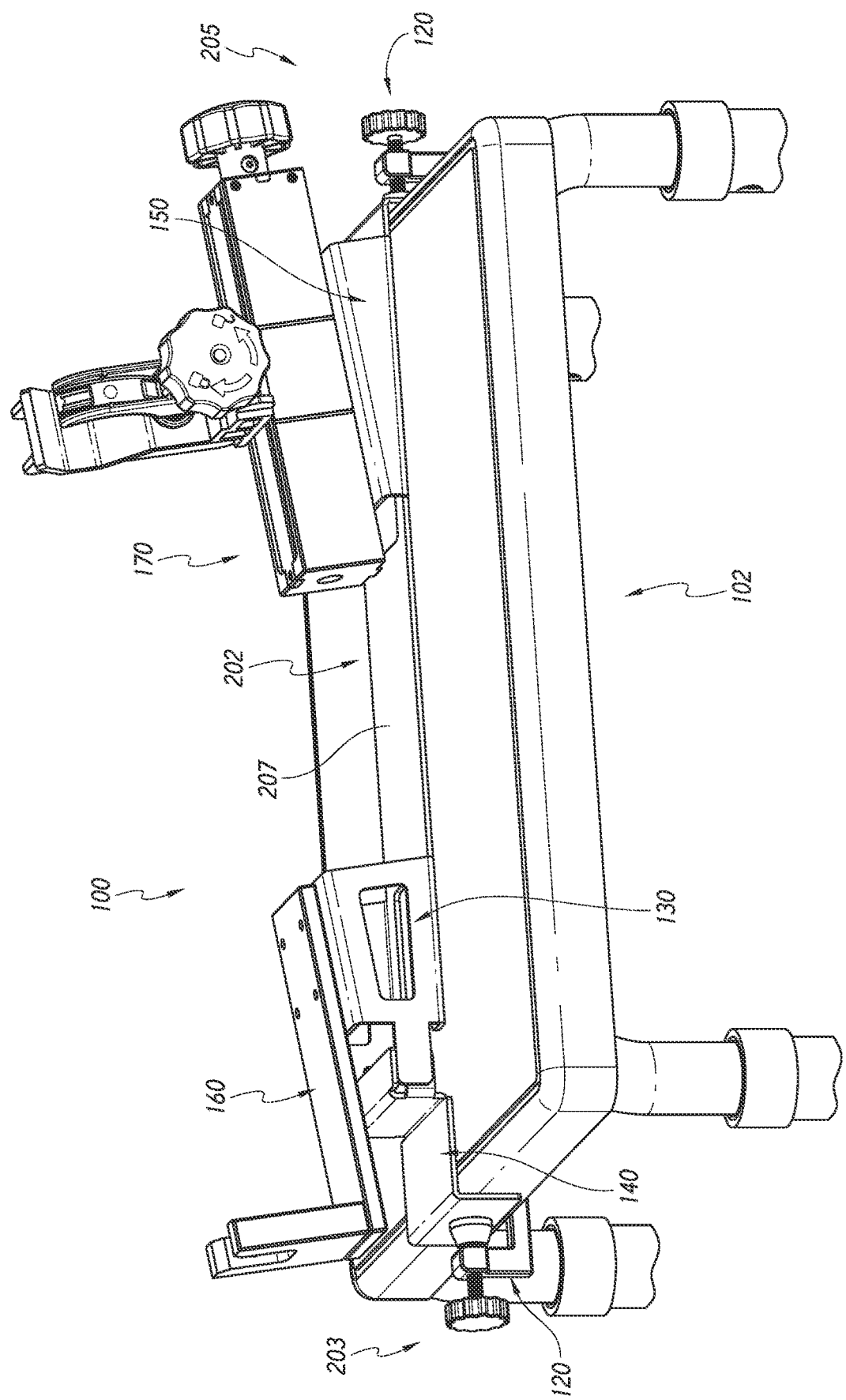

FIGS. 1A-1B illustrate an embodiment of a stabilizer 100 which can be used to hold embodiments of a delivery system in proper position when using the delivery systems. Examples of delivery systems that may be held with the stabilizer are described in detail in U.S. Pat. Pub. Nos. 2017/005616, 2016/0317301, 2017/005617, and 2019/0008640, the entirety of each of which is hereby incorporated by reference in its entirety. The disclosed stabilizer 100 can be advantageous for a transseptal (e.g., transfemoral) approach for delivering a replacement heart valve by allowing for fine motor control of a delivery system within the stabilizer. However, the embodiments of the stabilizer 100 disclosed herein can be used for other approaches and other procedures as well, such as transapical approaches, and are not so limited to replacement heart valves.

Generally, the stabilizer 100 (e.g., system, stabilizer system, stabilizer station) can be a system for use during an implant/surgical procedure, while including certain movable components. The stabilizer 100 can be used to hold a delivery system in place, for example above a patient's leg or on an operating table, though the particular position is not limiting. A delivery system, such as for delivering a replacement heart valve, can be locked into the stabilizer 100, as discussed below, which allows the delivery system to remain stable during the procedure. In some embodiments, the stabilizer 100 can be used to torque (rotate), advance, and/or retract components (independently or simultaneously) of the delivery system in a controlled manner. As shown in FIG. 1A, the distal end 203 of the stabilizer 100 can be the end closest to the delivery site (e.g., the patient or a location within the patient) where the proximal end 205 of the stabilizer 100 is located opposite the distal end 203.

Previously, delivery systems were held in place by an operator during the whole procedure. The operator would manually move the delivery system or components thereof, and thus accuracy of the delivery system movements is highly dependent on the stability and skill of the operator. If the operator moves the device unintentionally, then proper positioning of the system and associate implant could be lost and/or compromised. Further, if movements are intentional, but too gross, proper positioning could also be lost and/or compromised. Accordingly, embodiments of the disclosed stabilizer can provide for stability during operation of a delivery system.

Figure 2:
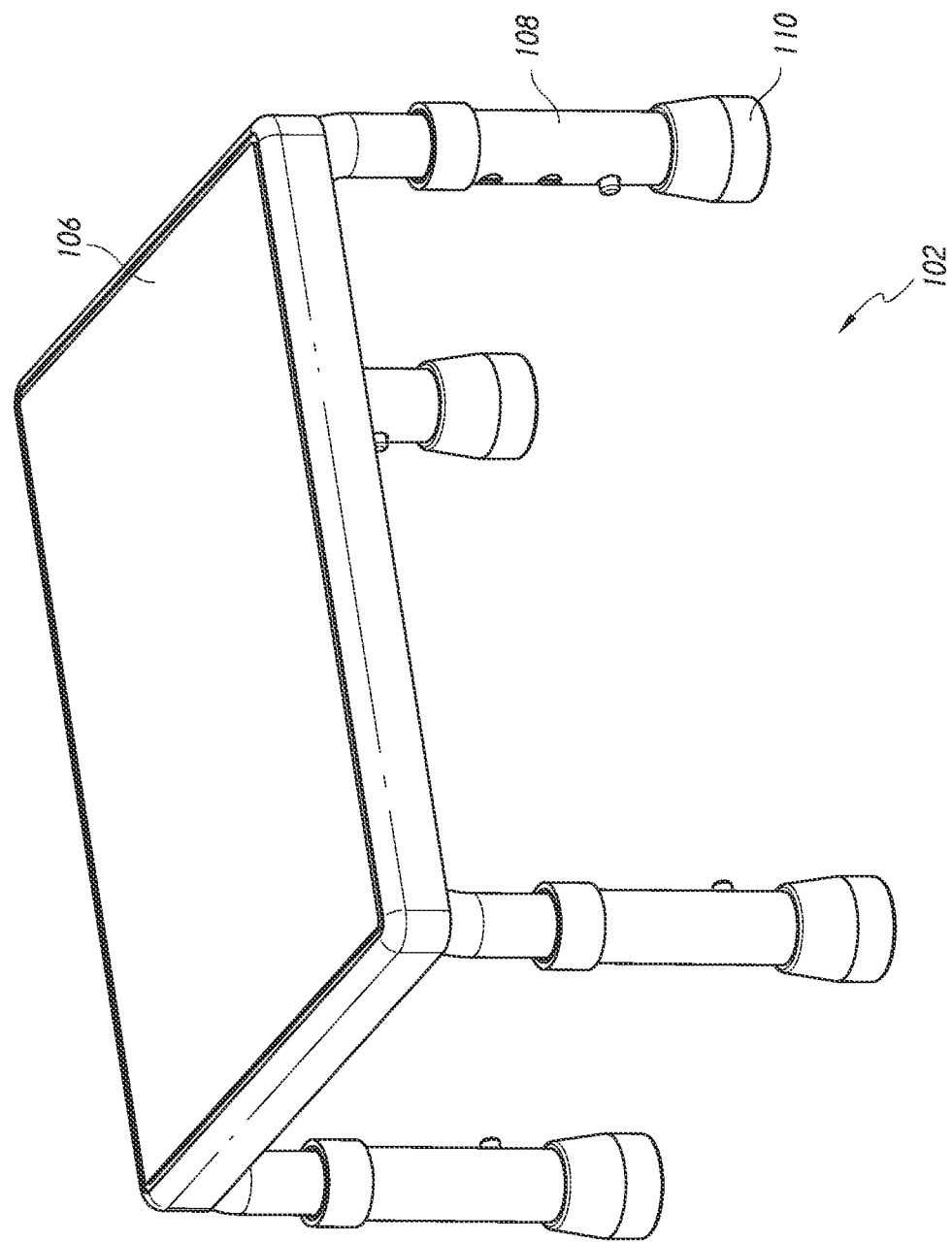
FIG. 2 illustrates an embodiment of a base which can be used with the stabilizer of FIG. 1.

In some embodiments, the disclosed stabilizer 100 is provided as part of a stabilizer system or stabilizer assembly that can also include a base, stool or other flat surface 102, such as shown in FIGS. 1B and 2. In some embodiments, the base 102 may not be used. In some embodiments, the base 102, such as shown in FIG. 2, can be, for example, placed over a patient's leg in order to help support the stabilizer 100. The base 102 can be sized to properly interact with the stabilizer 100. In some embodiments, the base 102 can include a generally flat upper surface 106 with a number of legs 108 extending downwards from that surface. Thus, a patient may extend their leg through gaps between adjacent legs 108 as needed. In some embodiments, 2, 3, 4, 5, 6, 7, or 8 legs can be used with the base 102. In some embodiments, the legs 108 can be adjustable in order to vary the height of the upper surface 106. The legs 108 can be separately or simultaneously adjustable. In some embodiments, the legs 108 can end in lockable wheels for transporting the base 102. In some embodiments, the legs 108 can end in padded or rubber ends 110, such as shown in FIG. 2, which can provide grip to the base 102. In some embodiments, the lockable wheels and rubber ends 110 may be removable and interchangeable from the legs 108. In some embodiments, the upper surface 106 may include one or more components for interacting with the stabilizer 100.

Figure 3:
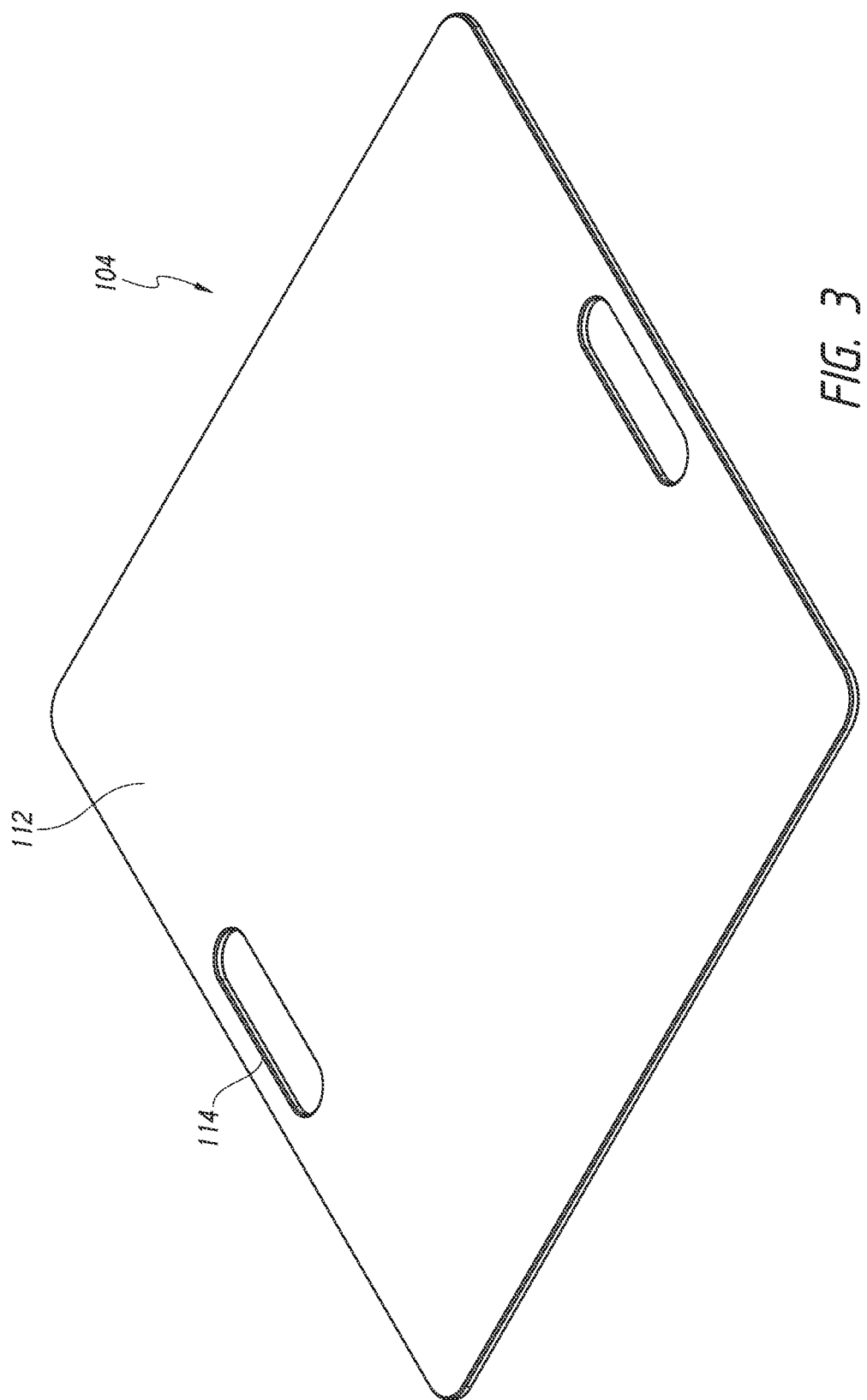
FIG. 3 illustrates an embodiment of a plate which can be used in conjunction with the base of FIG. 2.

In some embodiments, a stabilizer system can further include a plate 104 or other hard surface which can be placed under a patient for providing a stable surface 112 for the base 102 to be placed on, as shown in FIG. 3. In some embodiments, the plate 104 can be non-sterile. The plate 104 can be generally flat in some embodiments, or can have protrusions or other extensions. In some embodiments, the plate 104 can include cutouts 114 which can be used as handles for moving the plate. Further, the plate 104 can include indentations, divots, or apertures for receiving the legs 108 of the base 102. The plate 104 can be made of metal, plastic, or ceramic and the particular material does not limit the disclosure.

The plate 104 can rest on a table or other surface, such as an operating room table, beneath a patient's leg and can provide a rigid surface for the legs 108 of the base 102 to stand on. Thus, the base 102 can rest on top of the plate 104 to provide a raised, rigid surface for the stabilizer 100 above the legs. In some embodiments, the plate 104 and the base 102 can be non-sterile and can be located underneath a sterile drape. In some embodiments, the stabilizer 100 can be sterile and placed on top of a sterile drape.

In some embodiments, the plate 104 and/or the base 102 may not be used with the stabilizer 100.

The stabilizer 100 can be attached to the base discussed above, or other table such as an operating table, through the use of one or more clamps 120, shown in detail in FIGS. 1A-1B. In some embodiments, the base 102 and plate 104 discussed above may not be used in the stabilizer 100, and the stabilizer 100 can be attached directly to a table or other flat surface.

Figure 5:
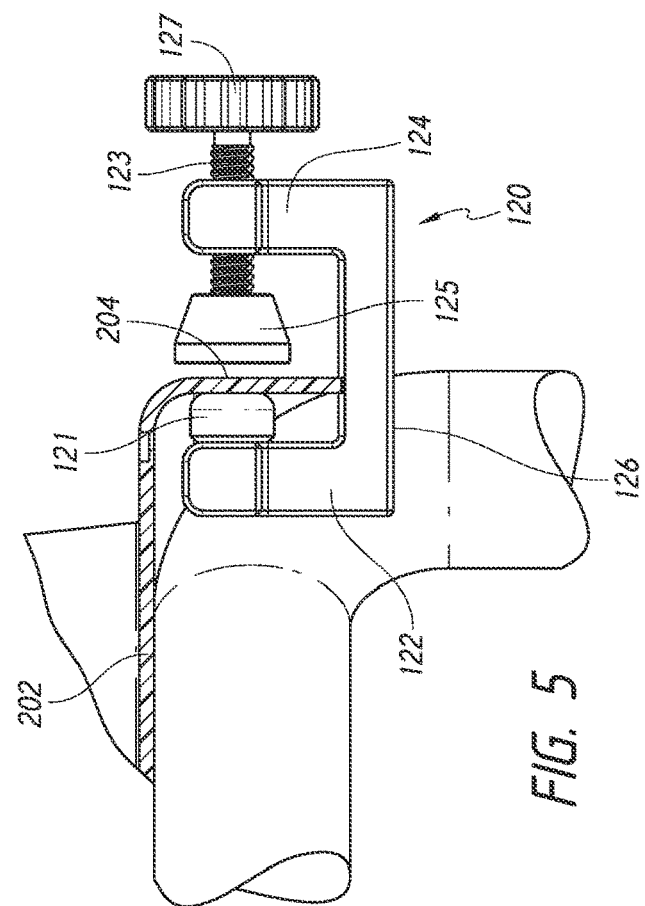
FIGS. 4-5 illustrate embodiments of clamps which can be used with a stabilizer.
Figure 4:
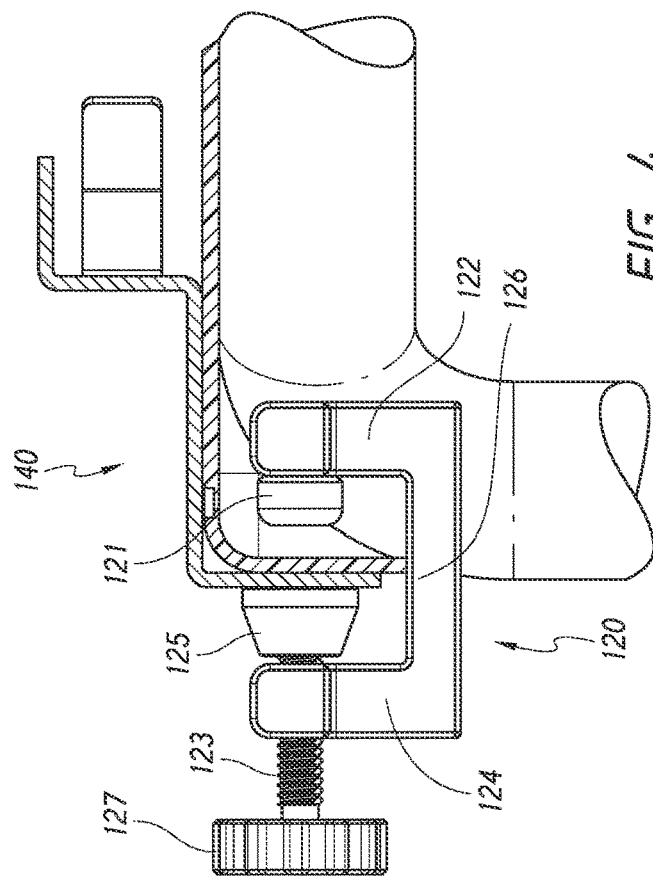

FIGS. 4-5 illustrate embodiments of a clamp 120 attached at a distal end (FIG. 4) and a proximal end (FIG. 5) of the stabilizer 100. Advantageously, embodiments of the disclosed clamp 120 can be a one-piece clamp, though other types of clamps can be used as well. In some embodiments, the clamp 120 can be a sterilizable c-clamp. Further, the clamp 120 can be low profile so that it does not interfere with the patient's leg or the operating field. The clamp 120 can include all or mostly all rounded/atraumatic surfaces so as not to break any sterile field that has been used during operation. Thus, the clamp 120 may not include any sharp corners as shown in FIGS. 4-5.

As shown in FIGS. 1A-1B, the stabilizer 100 can be attached to the base 102 (or other flat surface) using two clamps 120, one at a proximal end and one at a distal end, though other numbers of clamps can be used, such as 1, 2, 3, 4, or 5 clamps. In some embodiments, the clamps 120 can be the same. In some embodiments, there can be differences between clamps 120. In some embodiments, the clamps 120 can be removable from the stabilizer 100. In some embodiments, the clamps 120 can be permanently connected to the stabilizer 100. In some embodiments, the clamps 120 have no sharp edges, which can allow them to be compatible with a sterile drape placed over the base 102 to avoid tearing. The clamps 120 themselves can be spaced on generally opposite sides of the stabilizer 100 (either lengthwise or widthwise). In some embodiments, the clamps 120 can be physically attached to the stabilizer 100. In some embodiments, the clamps 120 can be removable or movable on the stabilizer 100, thus allowing them to be moved to an optimal clamping position.

As shown in FIGS. 4-5, the clamp 120 can be formed of two spaced-apart legs, an inner leg 122 and an outer leg 124, connected by a connector leg 126, thereby forming a general C-shape or U-shape, though other shapes can be used as well. The inner and outer legs 122/124 can be generally the same size and shape, though they may be different shapes. They also may extend generally parallel to one another. The inner leg 122 may include a first pad 121 facing towards the outer leg 124. The first pad 121 may be rubber or other soft material (cloth, plastic, etc.). The outer leg 124 may accept a threaded screw/bolt 123 between a second pad 125 and a handle 127 for tightening the clamp 120, such as through an aperture (threaded or unthreaded) in the outer leg 124. Thus, a portion of the stabilizer 100 can be located and compressed between pads 121/125 in order to hold the stabilizer 100 in place. However, other clamps can be used as well and the particular clamp does not limit the disclosure.

Figure 6:
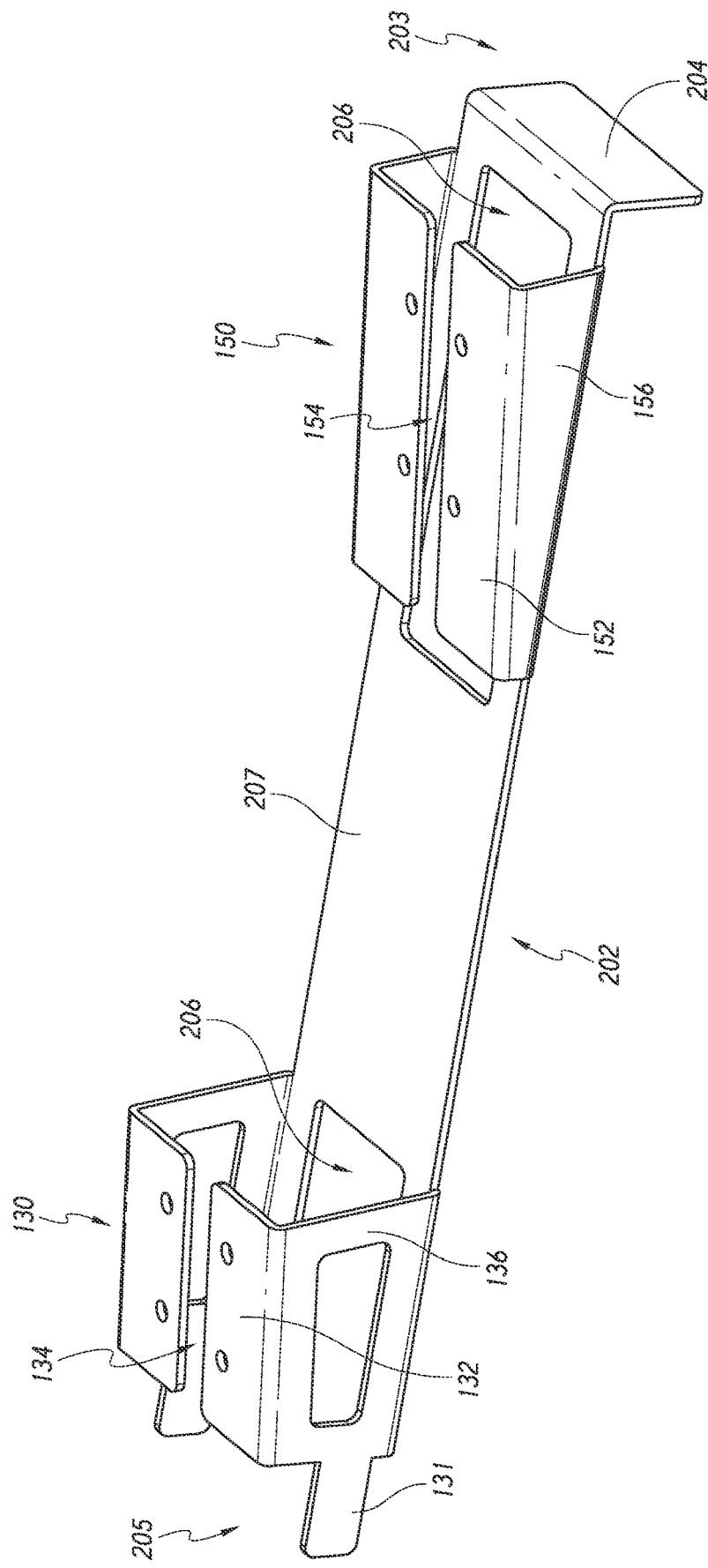
FIG. 6 illustrates embodiments of a stabilizer main body with certain components removed.

As shown in FIG. 6, with some components removed for convenience, the stabilizer 100 can include a main body 202 (or elongated main body). The main body 202 can be generally rectangular in shape, though the particular shape is not limiting and other shapes, such as circles, triangles, etc., can be used as well. The main body 202 can include a longitudinal axis extending from the proximal end 203 to the distal end 205, such as generally along a center of the main body 202. The main body 202 can include some or all of the features disclosed below.

The main body 202 can include a generally flat elongated base plate 207, a first angled section 130, and a second angled section 150. The main body 202 can have a generally flat bottom surface in order to lay flat on a surface, such as base 102 or other table surface. The main body 202 can include grooves, tabs, or other mechanical attachment components on a bottom surface, such as to improve frictional grip and prevent movement. In some embodiments, the proximalmost end of the main body 202 can include a flange (e.g., lip) 204 extending downwards. This flange 204 can extend over the edge of a base or surface, thereby allowing for proper positioning of the base 102. In some embodiments, the flange 204 can be hook shaped for wrapping around the edge of a surface. In some embodiments, the flange 204 may include some movement in order to lock onto different sized surface. Further, a clamp 120 can be attached to the flange 102, such as shown in FIG. 5, in order to hold the stabilizer 100 in place. In some embodiments, the main body 202 can also include a flange at the distalmost end to fully wrap around a table. In some embodiments, more than one flange 102 may be used on either end. In some embodiments, no flanges are used on either end of the stabilizer 100.

In some embodiments, the main body 202 can include one or more cutout sections 206, such as seen in FIG. 6. This can generally reduce the weight of the stabilizer 100. However, in some embodiments the main body 202 does not include the cutouts. The cutouts 206 can be rectangular, circular, triangular, or any shape. In some embodiments, the main body 202 can include two cutouts 206, one at a proximal end 203 and one at a distal end 205. The cutout 206 at the distal end 205 can extend to the distalmost end of the stabilizer 100 and thus the cutout may not be fully surrounded by the stabilizer 100.

As shown in FIG. 6, the main body 202 can include a first angled section (e.g., distal angled section, sheath holder) 130 and a second angled section (e.g., proximal angled section, handle holder) 150. The first angled section 130 is distal to the second angled section 150. The first angled section 130 has an angled surface and the second angled section 150 has an angled surface. In some embodiments, the distal angled surface (e.g., on the first angled section 130) is configured to hold a sheath (such as an integrated sheath) of a delivery system stationary while the handle of the delivery system can be held on the second proximal angled surface (e.g., on the second angled section 150) and can move in and out relative to the sheath (e.g., the delivery system moves through the stationary held sheath). Holding the sheath stationary prevents unintended sheath movement, for example in and out of the femoral vein, decreasing trauma and potentially decreasing blood loss. Additionally, embodiments of the disclosed stabilizer 100 can have a low profile and be angled for optimized access of a patient, such as optimized femoral access.

The first angled section 130, which is provided at or near the distal end 205 of the base 207, is shown in greater detail in FIGS. 7-8. The angled section 130 can be generally angled downwards towards the distal end. As shown, the angled section 130 can include an upward facing angled surface 132, which is raised from the base plate 207 and which can be at a particular angle from the flat main body 202. For example, the angle can be 1, 2, 3, 4, 5, 6, 7, 8, 9, 10, 15, 20, 25, 30, 35, 45, or 50° with respect to the main body 202. In some embodiments, the angle can be between 5 and 30° (or between about 5 and about 30°). In some embodiments, the angle can be between 5 and 15° (or between about 5 and about 15°). The upward facing angled surface 132 can be flat, or generally flat. In some embodiments, the angle of the upward facing surface 132 can be adjustable, such as through knobs, screws, motors, or other electric controls. In some embodiments, the angle can be fixed in one position. Further, the upward angled surface 132 can be rotated around a vertical axis to provide further repositioning. In some embodiments, the upward facing surface 132 can include a slot 134 extending generally proximally to distally (e.g., generally parallel to the longitudinal axis of the stabilizer 100) for attachment of the hub nest 160, described further below.

The upward facing surface 132 can be attached to the main body 202 by a pair of walls 136, as shown in FIG. 7-8. In some embodiments, the pair of walls 136 include apertures 138, though in some embodiments the pair of walls 136 does not include any apertures. Other shapes and designs can be used as well, such as rounded surfaces, generally half-spherical surfaces, etc., and the shape is not limiting.

Each or the pair of walls 136, though in some embodiments only one of the pair of walls 136, may include distally extending tabs/extensions 131. The tabs 131 can be generally rectangular in shape, but the particular shape is not limiting. The tabs 131 can be configured to mate or dock with a base adapter 140 for attachment of the stabilizer 100 to a table. In some embodiments, the upward facing surface 132 may be attached to the main body 202 by a proximal back wall, but some embodiments may not use a proximal back wall.

The base adapter (e.g., dock) 140 shown in FIGS. 7-8 can be a separate piece from the rest of the stabilizer 100, though in some embodiments can be connected. A separate base adapter 140 allows the base adapter 140 to be attached/clamped/set up prior to operation of the stabilizer 100. Thus, when the delivery system is ready to be used, a distal end of the main body 202 can insert into the base adapter 140, such as a proximal end of the base adapter 140, quickly and only one clamp is required to finalize the position. The base adapter 140, once attached to a surface, provides features for the stabilizer 100 to slide into, discussed in detail below. When the stabilizer 100 is secured into the base adapter 140, and all clamps 120 are attached, the base adapter 140 prevents the stabilizer 100 from lifting away. FIG. 7 illustrates the base adapter 140 connected to the main body 202 and FIG. 8 shows the base adapter 140 and the main body 202 separated. While the base adapter 140 is shown attached at the distal end of the stabilizer 100, it can instead be located on the proximal end. In some embodiments, two base adapters can be used, one on each end. In some embodiments, the base adapter 140 can be connected to the stabilizer 100, but can include adjustable features such as ratcheting, clamping, etc. to attach to a table.

As shown in FIG. 7-8, the base adapter 140 can include a downward facing flange 142 at its distalmost end. The downward facing flange 142 can be used to attach a clamp 120 to the table, such as shown in FIG. 4. However, a flange may not be used in some embodiments. In some embodiments, the flange 142 may be a hook shaped for wrapping around a surface. Moving proximally from the flange 142, the base adapter 140 can include a generally flat base surface 144 followed by a docking feature 146. The docking feature 146 can include an upwardly extending surface 148 with a top surface (or tab) 141 and two flanges (or tabs) 143 extending proximally from the upwardly extending surface 148. The tabs 131 discussed above can mate with the flanges 143. For example, the flanges 143 may be able to flex outwards to receive the tabs 131 and thus provide a frictional force on the tabs 131. Further, the tabs 131 may be inserted between the flanges 143 in order to abut against the upwardly extending surface 148 on their distal ends, thus docking the tabs 131 with the docking features as shown in FIG. 7. Thus, the top surface 141 prevents vertical motion of the tabs 131, preventing removal. In some embodiments, screws, bolts, tabs, etc. can be used to removably attach the tabs 131 to the docking features 146. This is one example of a base adaptor 140 but other base adapters may be used as well. Further, a base adapter 140 may not be used and the stabilizer 100 can attach directly to a surface.

Figure 9:
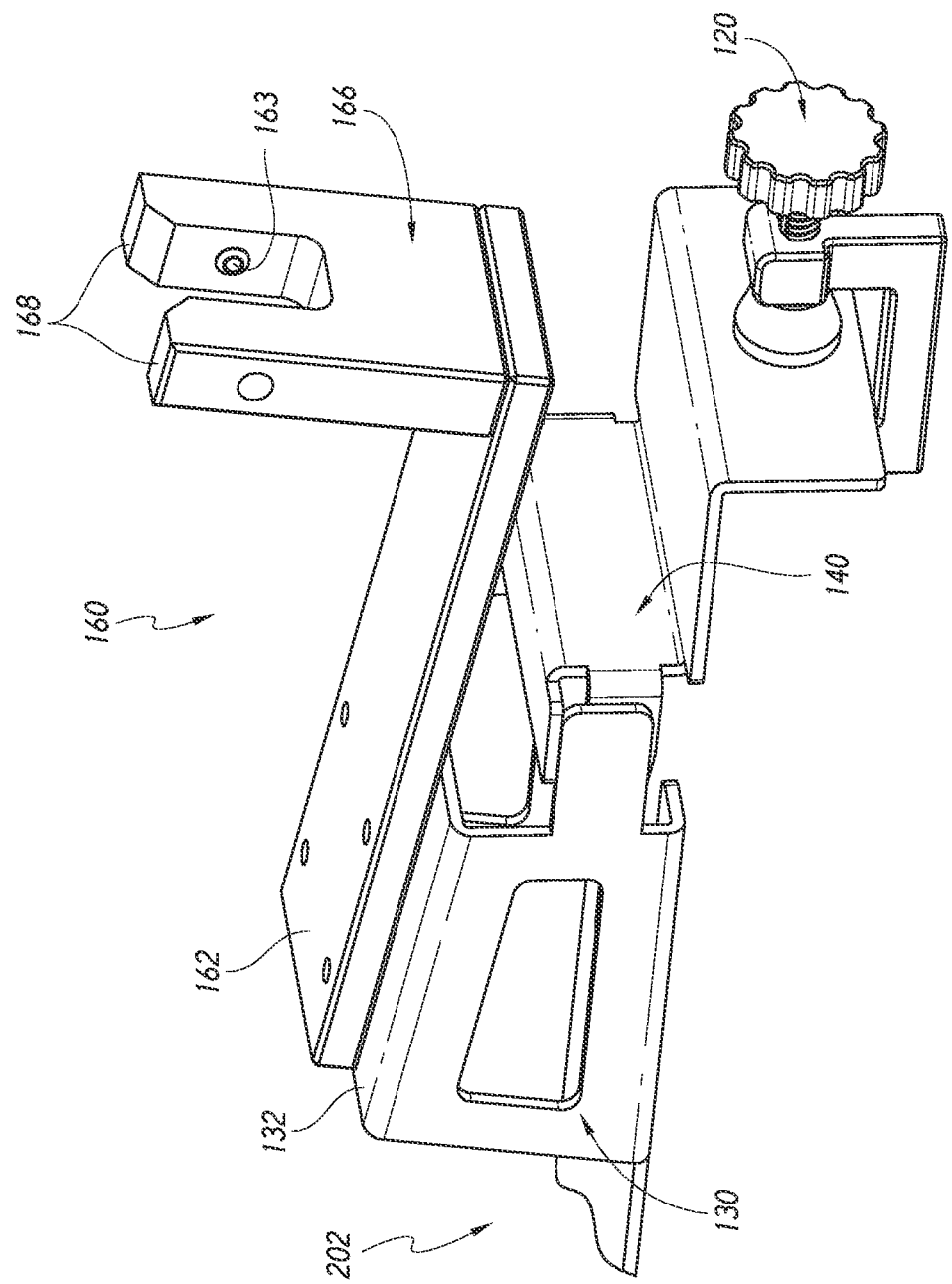
FIGS. 9-11 illustrate embodiments of a hub nest assembly.
Figure 10:
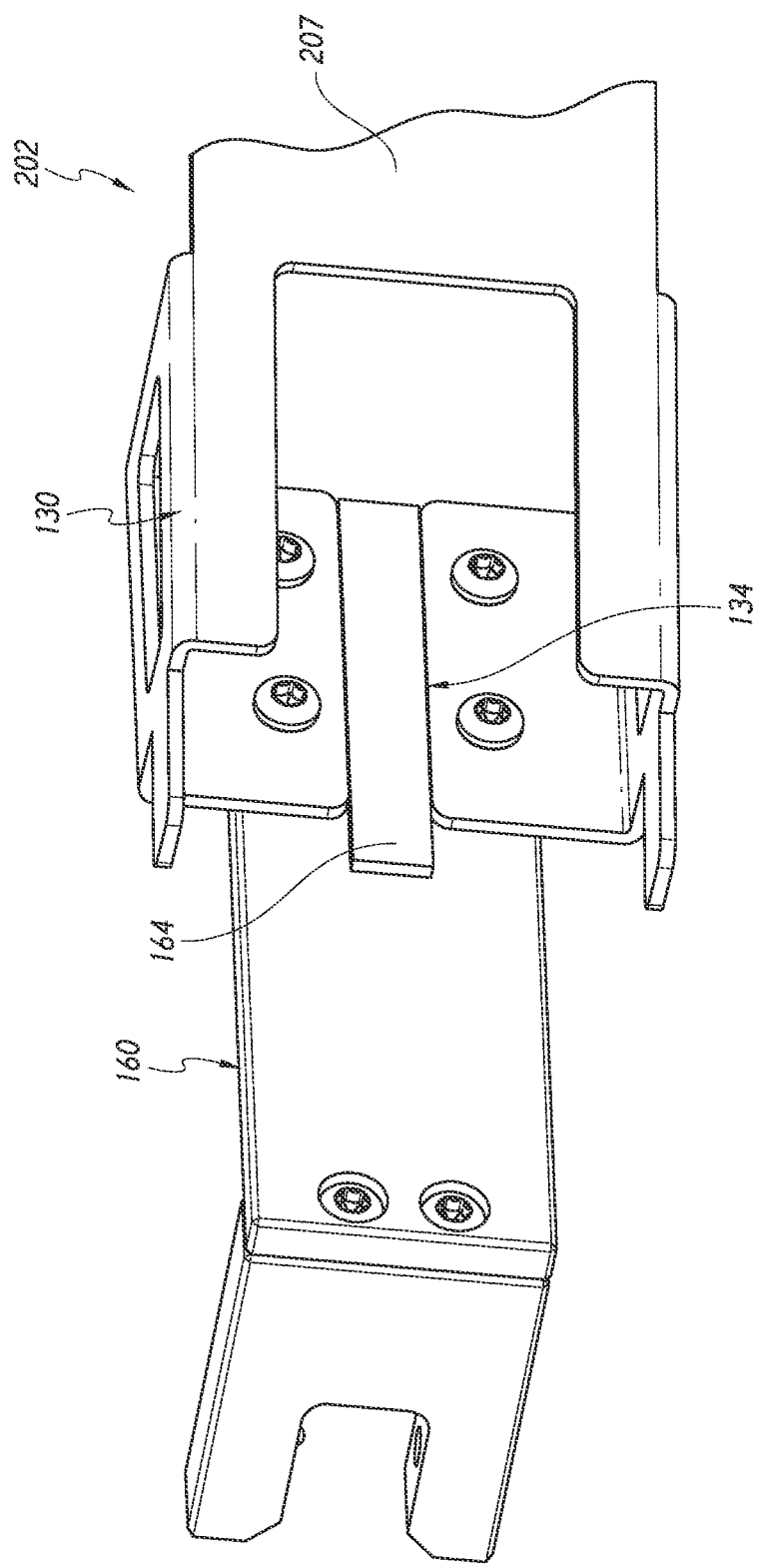
Figure 11:
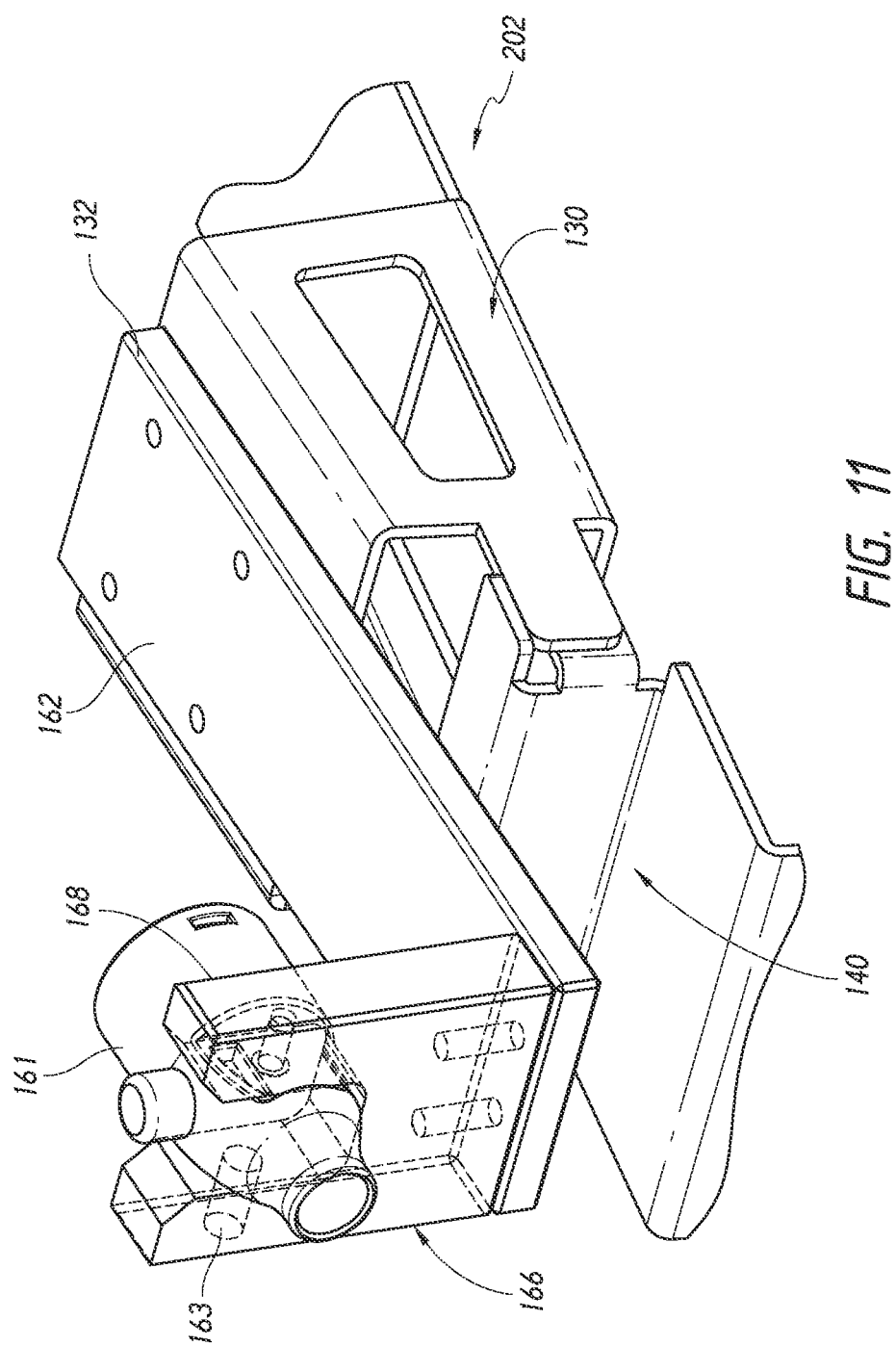
Figure 12:
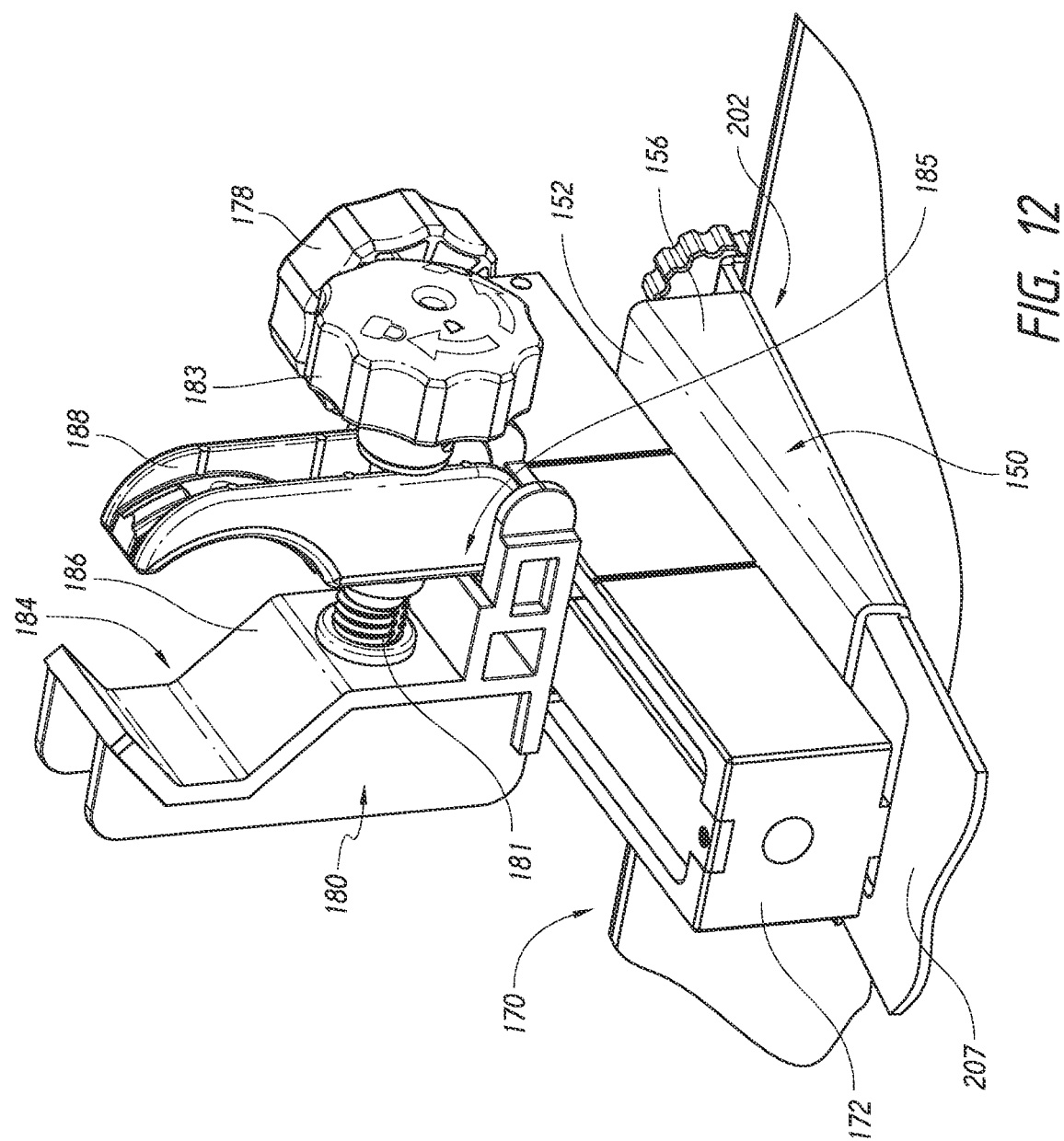
FIGS. 12-14 illustrate embodiments of a linear clamp assembly.
Figure 13:
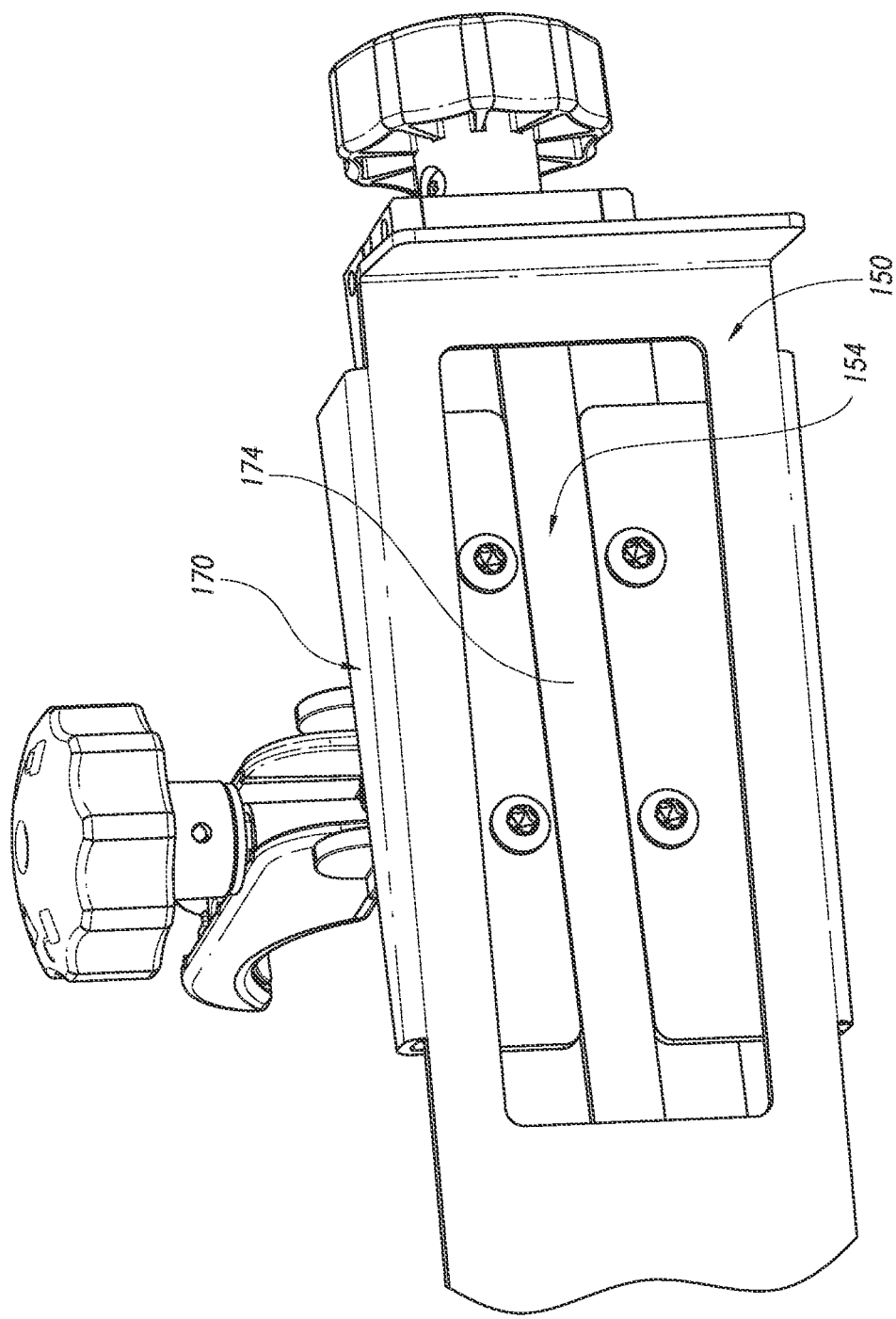
Figure 14:
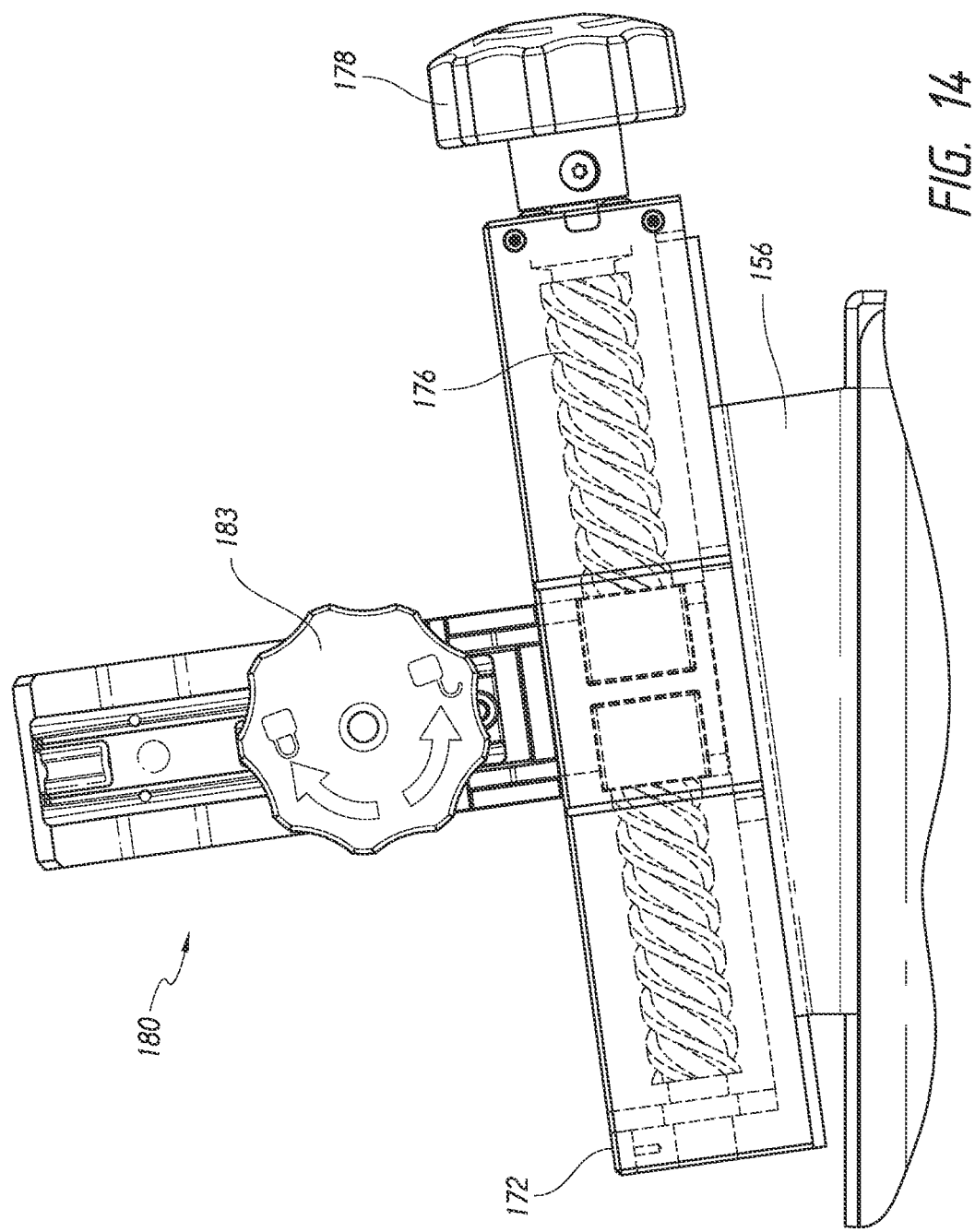

Moving proximally on the stabilizer 100, FIGS. 9-11 illustrate an embodiment of a hub nest assembly or guide assembly 170. Attached to upward facing surface 132 is a hub nest assembly 160. The hub nest assembly 160 can include a generally rectangular hub nest adapter 162 which can rest at least partially on the upward facing surface 132.

The hub nest adapter 162 can further include a downward facing longitudinal tab 164, such as shown in FIG. 10, configured to mate with the slot 134 on the upward facing surface 132. In some embodiments, the hub nest adapter 162 can be moved along the slot 134 and attached to the upward facing surface 132 for proper positioning of a delivery system within the stabilizer 100.

Generally at the distal end of the hub nest adapter 162 is the hub nest 166, though the position is not limiting. In some embodiments, the hub nest 166 attaches directly to the upward facing surface 132 and the hub nest adapter 162 is not used. The hub nest 166 can extend upwards from the hub nest adapter 162 and can therefore be angled with respect to the main body 202 of the stabilizer 100. The position and angle of the hub nest adapter 162 can be adjusted in some embodiments. The hub nest 166 can include a pair of upwardly extending arms 168 which are configured in some embodiments to mate with a sheath hub of the delivery system which is connected to the rigid live-on (or integrated) sheath. An example of such a sheath hub 161 is shown in FIG. 11. The sheath hub 161 may be attached to the hub nest 166 prior to attachment of the delivery system, or can be attached during attachment of the delivery system. In some embodiments, the upward extending arms 168 can releasably mate with another component of the delivery system, such as a distal portion of a handle or an outer sheath assembly of a delivery system. In some embodiments, the upwardly extending arms 168 can include spring plungers 163 on one or both of the arms 168 in order to lock the sheath hub 161 in place. Further, the spring plungers 163 can allow for rotational motion of the sheath hub 161 with respect to the hub nest 166. However, other attachment methods can be used as well, and the particular attachment is not limiting. In some embodiments, the hub nest 166 can include a mating detent for the sheath hub. This can provide for tactile feedback to a user. Advantageously, the hub nest 166 can hold the sheath hub 161 stationary during the surgical procedure and prevents unnecessary moving. This can minimize trauma to the access site.

The second angled section 150, which is provided at or near the proximal end 203 of the main body 202, is shown in greater detail in FIGS. 12-15C. The angled section 150 can be generally angled downwards towards the distal end. As shown, the angled section 150 can include an upward facing angled surface 152, which is raised from the base plate 207 and which can be at a particular angle from the flat main body 202. For example, the angle can be 1, 2, 3, 4, 5, 6, 7, 8, 9, 10, 15, 20, 25, 30, 35, 45, or 50°. In some embodiments, the angle can be between 5 and 30° (or between about 5 and about 30°). In some embodiments, the angle can be between 5 and 15° (or between about 5 and about 15°). The upward facing angled surface 152 can be flat, or generally flat. In some embodiments, the angle of the upward facing surface 152 can be adjustable, such as through knobs, screws, motors, or other electronic controls. In some embodiments, the angle can be fixed. Further, the upward angled surface 152 can be rotated around a vertical axis to provide further repositioning.

In some embodiments, the upward facing surface 152 can include a slot 154 extending generally proximally to distally. Further, as shown the upward facing surface 152 can be attached to the main body 202 by a pair of sidewalls 156.

In some embodiments, the second angled portion 150 can be spaced away from the first angled portion 130, though alternatively they can be connected. In some embodiments, the first and second angled portions 130/150 are longitudinally aligned.

Further, as shown in the figures the second angled section 150 can have a height less than the first angled section 130. However, in some embodiments they can have the same height. In some embodiments the second angled section 150 can have a height greater than the first angled section 130. In some embodiments, the upward facing surface 152 of the second angled section 150 can be co-planar with the upward facing surface 132 of the first angled section 130. In some embodiments, the upward facing surface 152 of the second angled section 150 is not co-planar with the upward facing surface 132 of the first angled section 130. In some embodiments, the upward facing surface 152 of the second angled section 150 can be parallel with the upward facing surface 132 of the first angled section 130. In some embodiments, the upward facing surface 152 of the second angled section 150 is not parallel with the upward facing surface 132 of the first angled section 130. In some embodiments, the upward facing surface 152 of the second angled section 150 is parallel but not co-planar with the upward facing surface 132 of the first angled section 130.

On top of the second angled section 150, and mating with the slot 154, is the linear clamp assembly 170 shown in FIGS. 12-15C. The slot 154 can extend parallel, or generally parallel, to the longitudinal axis of the main body 202. If a patient were aligned perpendicular to the longitudinal axis of the main body 202, the linear clamp assembly 170 allows for medial/lateral adjustment. The linear clamp assembly 170 can include a delivery housing 172, which in some embodiments can comprise a housing generally shaped like a rectangular prism, though the shape is not limiting, with a longitudinally extending tab 174 on the bottom to mate with the slot 154, shown in FIG. 13. The track or housing 172 can be hollow to contain a travel screw 176, shown in FIG. 14. In some embodiments, the track or housing 172 further contains a handle or knob 178 for turning the travel screw 176. In some embodiments, there may be no housing containing the travel screw 176. In some embodiments, the angled section 150 can be unlocked from the base plate 207. This can allow the angled section 150, and the components on top, to slide relative to the base plate. This can allow for large adjustments to the handle carriage 180, allowing for the ability to readjust if a hard stop is hit.

A handle carriage 180 can interface with the travel screw 176, such as with a threaded aperture 182 that is located within the housing 172 and surrounds the travel screw 176. Thus, when the travel screw 176 is turned, such as by rotation of the knob 178, the handle carriage 180 will travel longitudinally (e.g., proximally to distally and distally to proximally) along the housing 172. The handle carriage 180 can travel 60, 70, 80, 90, 100, 110, 120, or 130 mm. In some embodiments, the handle carriage 180 can travel greater than 60, 70, 80, 90, 100, 110, 120, or 130 mm. In some embodiments, the handle carriage 180 can travel less than 60, 70, 80, 90, 100, 110, 120, or 130 mm. The travel along the travel screw 176 can be controlled using spring plungers which mate with detents on the knob 178. This can allow for detented, controlled travel of the handle carriage 180. Tactile feel of each "click" as the knob 178 turns can provide an operator tactile feedback for proper advancement along the travel screw 176, and can facilitate more controlled motion of the delivery system.

Figure 15A:
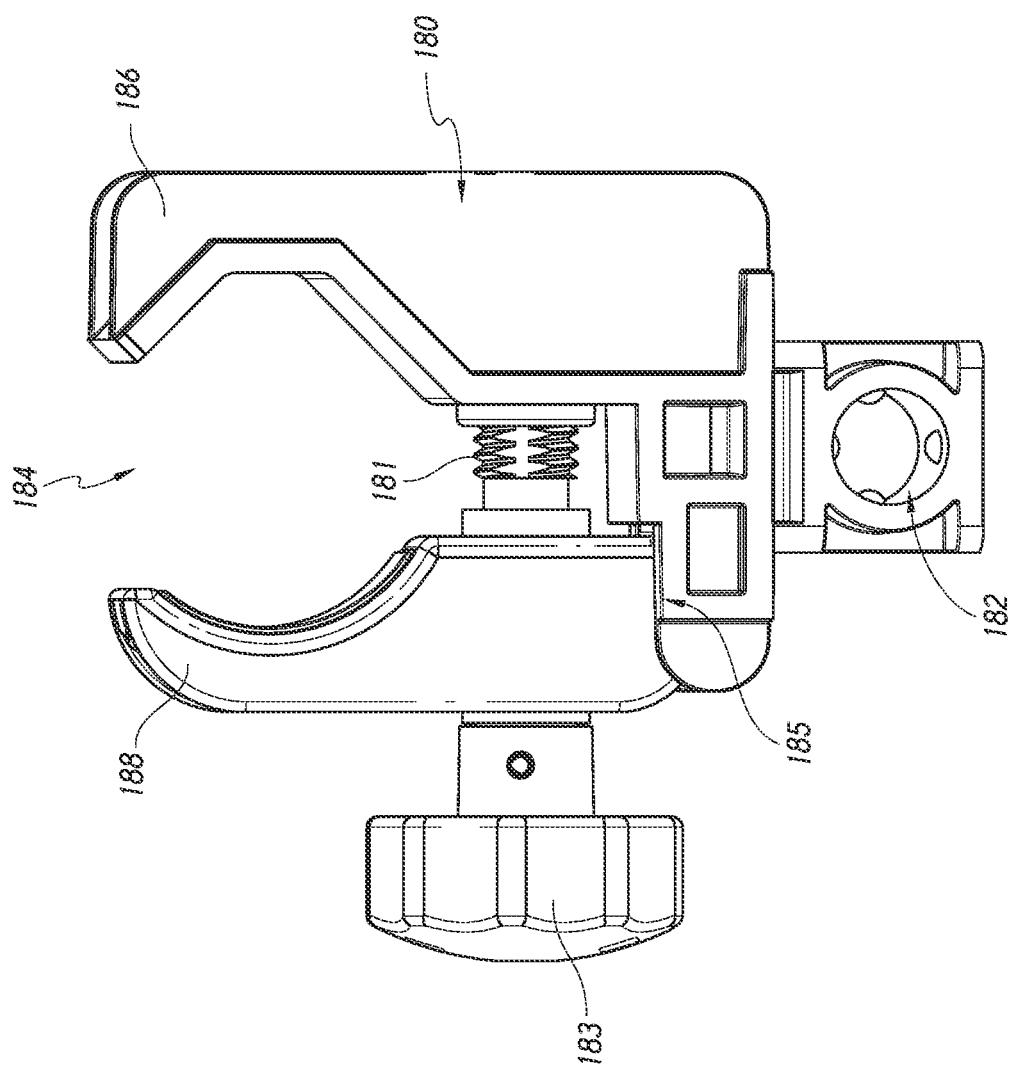
FIGS. 15A-15C illustrates embodiments of a clamp for a delivery system.

Attached at a top of the handle carriage 180 is a clamp 184, such as a padded or rubber overmolded clamp, shown in FIG. 15A. In some embodiments, the handle carriage 180 is integrally formed with a first half of the clamp 184. In some embodiments, the handle carriage 180 is separately formed from the clamp 184. The first half of the clamp 186 can be relatively stationary with respect to the handle carriage 180, such as if they are integrally formed. The second half of the clamp 188 can be connected to the first half of the clamp 186, such as through a screw or bolt 181. A knob 183 can therefore be used to tighten or loosen the two clamp halves 186/188. In some embodiments, the second clamp half 188 can be held within a slot 185 in the first clamp half 186 to prevent rotation of the second clamp half. The clamp 182 can be sized and configured to hold a handle of a delivery system. Further, the clamp 182 can resist rotational forces applied to the delivery system, such as knob rotational forces.

Figure 15B:
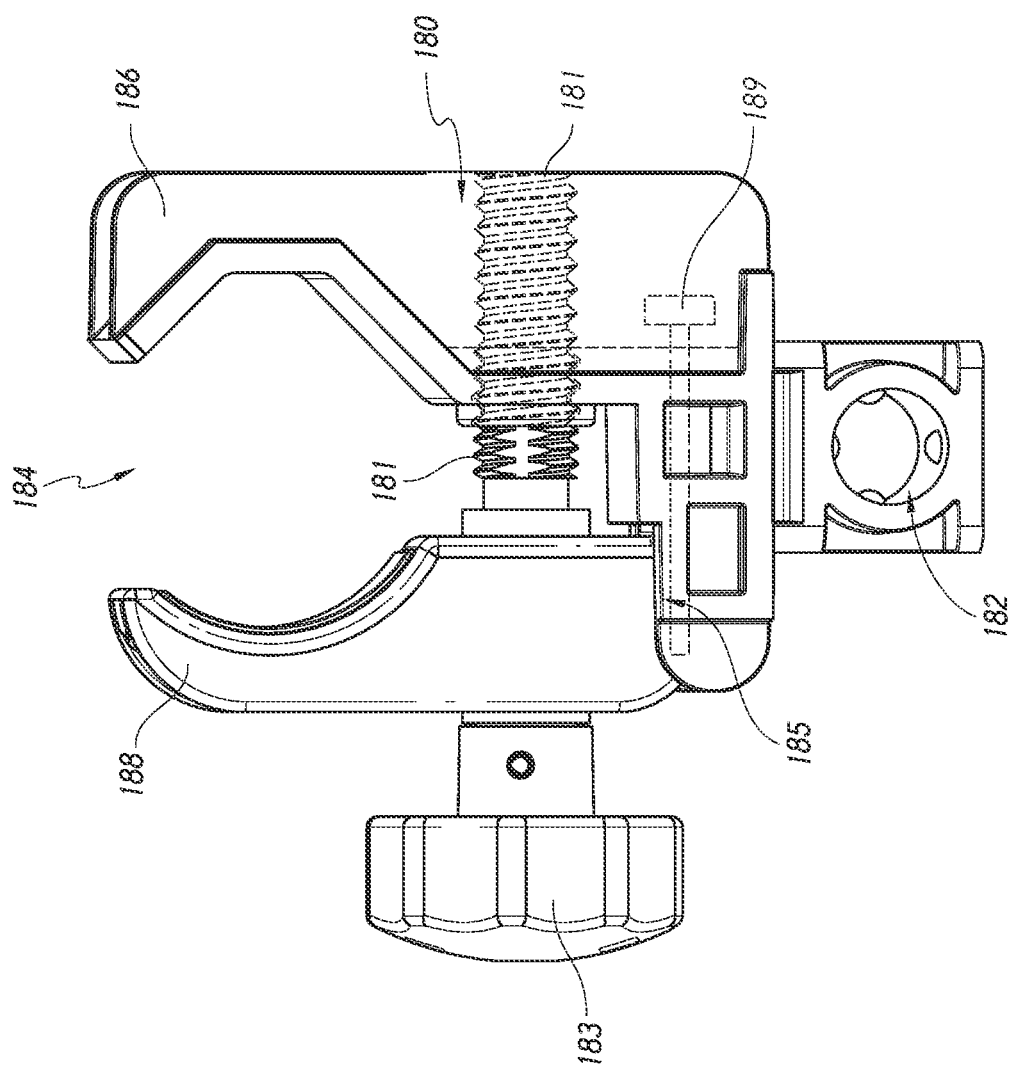

FIG. 15B illustrates further details of the handle carriage 180 of FIG. 15A. As shown, the internal cavity of first clamp half 186 can include female threading all the way through. Once the bolt 181 is threaded as far as possible, the top of clamp half 188 can bend inwards towards half 186 in a fulcrum motion to further compress any delivery system held within. The handle carriage 180 can further include a pin 189 which can extend through clamp 186 and be press fit into clamp 188. The pin 189 is press fit into the padded half to prevent release by too much unthreading, and therefore acts as a "hard stop" to prevent half 188 from being released.

Figure 15C:
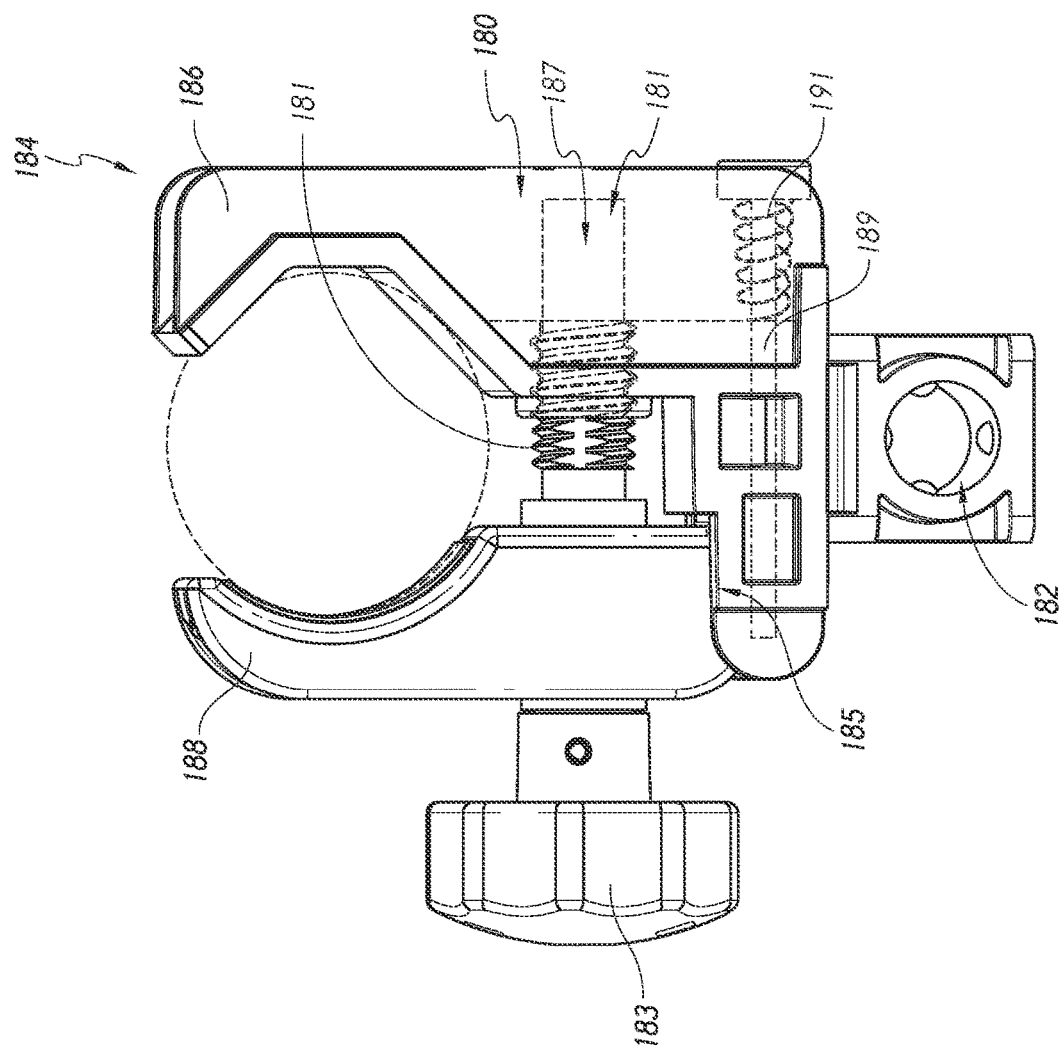

FIG. 15C illustrates an alternate embodiment of the handle carriage 180 shown in FIG. 15B. As shown, the female threading does not extend all the way through half 186, and therefore has an unthreaded cavity 187. This allows the bolt 181 to slide within that cavity 187 without turning, allowing for a quicker release when opening. Further, the handle carriage 180 can include pin 189 which can extend through clamp 186 and be press fit into clamp 188, again preventing accidental release. The pin 189 can include a spring 191. When the half 188 is pulled away, the spring 191 is compressed. Once half 188 is released, the spring 191 uncompresses to quickly bring half 188 towards half 186, similar to a pinball machine handle. When the spring 191 is at the neutral position, the clamp 184 may be docked on a delivery system (such as indicated by the dashed circle), but not fully locked.

In some embodiments, the threading can be replaced with a quarter turn quick locking design. Thus, the bolt 181 can include protrusions on one end, and the half 186 can include a mating feature for the protrusions. The bolt 181 can then be push inserted and rotate a quarter turn so the protrusions fit within the mating feature, preventing further motion. The bolt 181 can be released by turning the bolt 181 so that the protrusions can slide out of the half 186.

Figure 16:
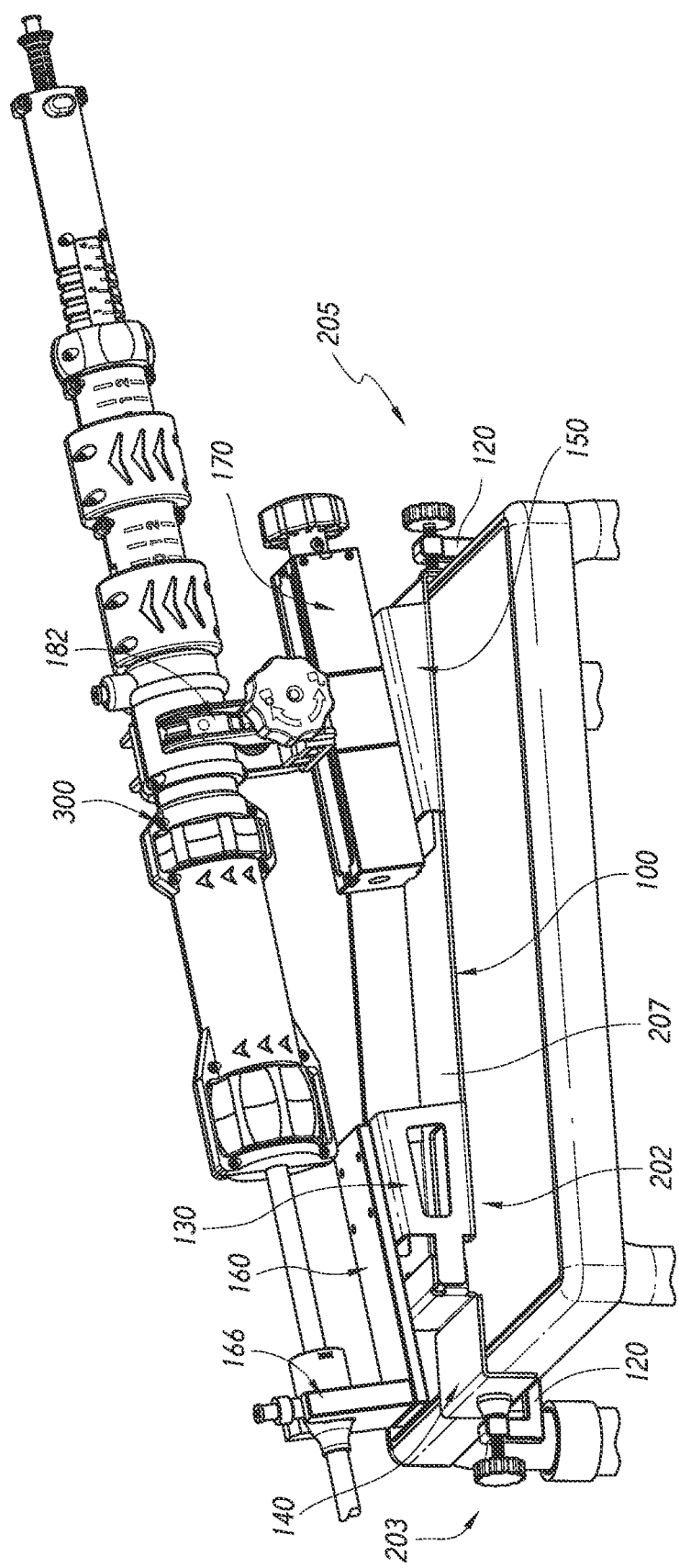
FIGS. 16-18 illustrate an embodiment of a stabilizer with a delivery system held within the stabilizer in different positions.
Figure 17:
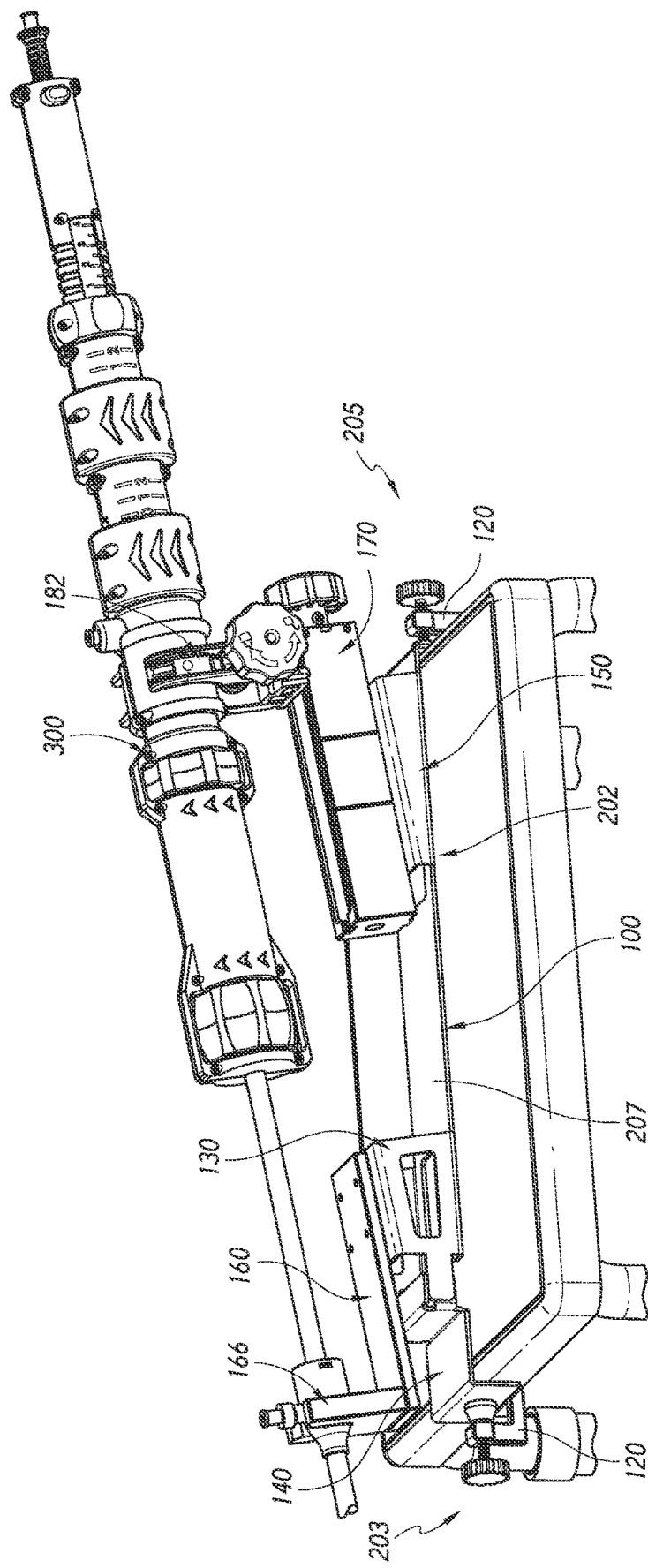
Figure 18:
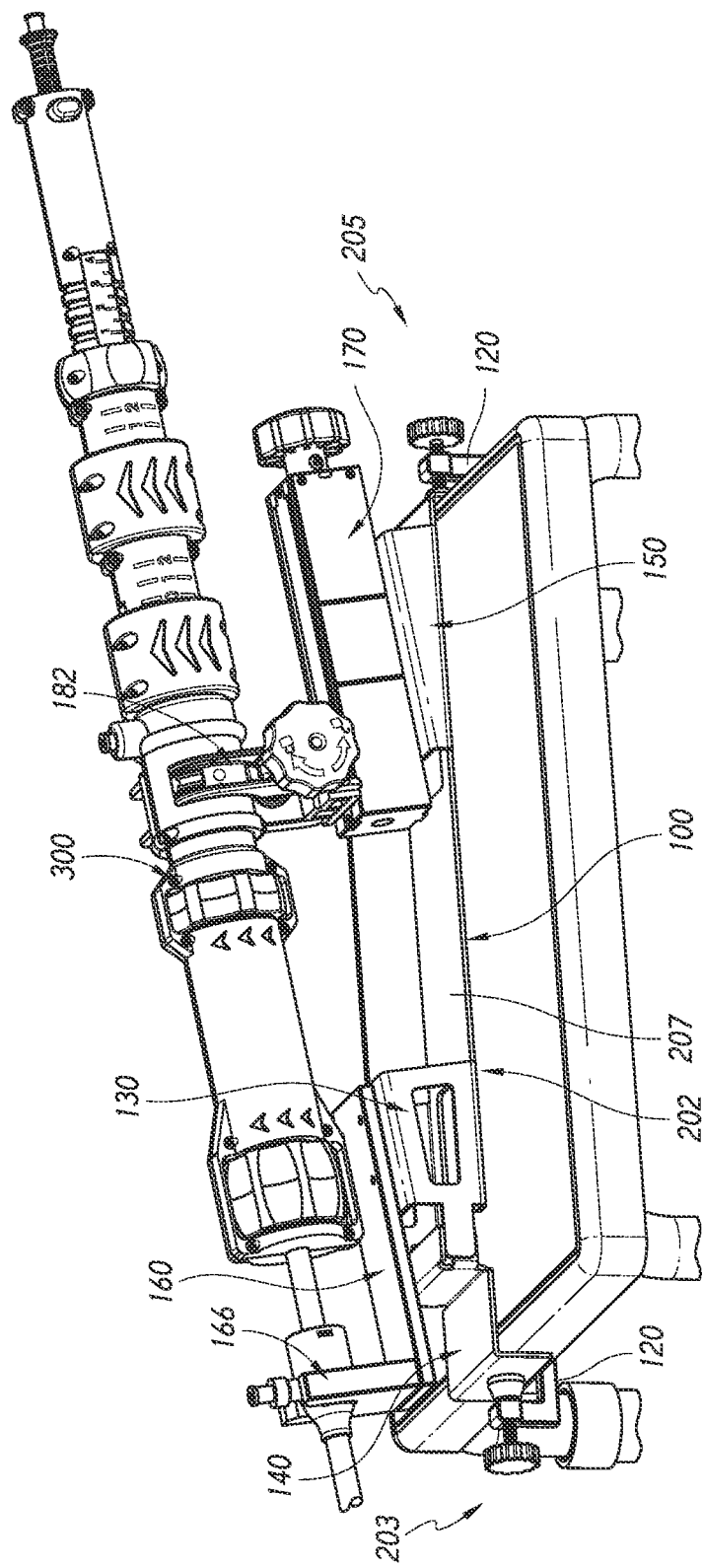

Accordingly, the clamp 182 and the hub nest 166 can be generally longitudinally and/or angularly aligned and angled downwards towards a distal end of the delivery system, which is shown attached in FIGS. 16-18. Thus, the delivery system handle 300 can be held within the clamp 182 and the hub nest 166. FIG. 16 illustrates an intermediate position of the delivery system, while FIG. 17 illustrates the proximalmost position of the delivery system and FIG. 18 illustrates the delivery system in the distalmost position.

Method of Operation

Disclosed is a method of operation of embodiments of the disclosed stabilizer 100 for delivering a replacement heart valve, in particular a replacement mitral valve. This can be particularly useful for a transseptal approach, but the stabilizer can be utilized with other approaches as well, such as transapical, and other heart valves, such as aortic. Further, the stabilizer 100 can be used for other medical procedures, and is not limited to replacing heart valves.

First, the base adapter 140 can be clamped to a surface, such as a table or the base 102 discussed above. The table can be located over or next to a patient. In some embodiments, the patient can be aligned generally perpendicular to the stabilizer 100. In some embodiments, the patient can be aligned generally parallel to the stabilizer 100. In some embodiments, the patient can be aligned at any angle between being parallel or perpendicular to the stabilizer 100.

Next, a distal portion of the main body 202 can be inserted into the base adapter 140 to dock the main body 202 with the base adapter 140. This can allow the main body 202 to be quickly located into the proper position as the base adapter 140 is already clamped down. Additionally, the base adapter 140 can allow for the stabilizer 100 to be used on different sized surface as there is some space within the base adapter 140. Thus, if the surface is long, the main body 202 may only be inserted a small amount into the base adapter 140. However, if the surface is shorter, the main body 202 may be inserted into the base adapter 140 as far as it can go.

Following, a proximal end of the main body 202 can be clamped to the surface. The delivery system may be attached into the main body 202 as discussed below prior to insertion of the main body 202 into the base adapter 140. However, in some embodiments the delivery system is attached after the main body 202 is inserted into the base adapter 140. The clamps and docking procedure can further provide gripping and stability.

For attachment of the delivery system, the distal end of the delivery system can be slid through the sheath hub 161 so that the delivery system extends distally from the stabilizer 100. The sheath hub 161 can rotate within the hub nest 166 in order to facilitate insertion of the delivery system. In some embodiments, the sheath hub 161 is already on the delivery system and the sheath hub 161 is then clicked into place in the stabilizer 100. Once inserted into the sheath hub 161, the handle of the delivery system can then be placed into the clamp 184. The clamp 184 can be adjusted in position using knob 178 in order to properly place the clamp 184 on the handle. This can be done to avoid any interference with any actuators on the handle. In some embodiments, the handle may include a specific slot or area for attachment of the clamp 184. The clamp 184 can then be tightened and held in place within the stabilizer 100.

Using knob 178, the handle of the delivery system can be finely controlled and advanced/retracted along the linear clamp assembly 170 for proper advancement within a patient (such as from the proximal position of FIG. 17 to the distal position of FIG. 18). When used in a transseptal approach for a replacement mitral valve, translating the delivery system using knob 178 can advance/retreat the distal end of the delivery system axially (or generally axially) with respect to the native mitral valve. The lower angles used in the stabilizer 100 can make the delivery system easier to use during the procedure. Once the operation is completed, the delivery system can be removed from the stabilizer 100.

Universal Stabilizer System

Figure 19:
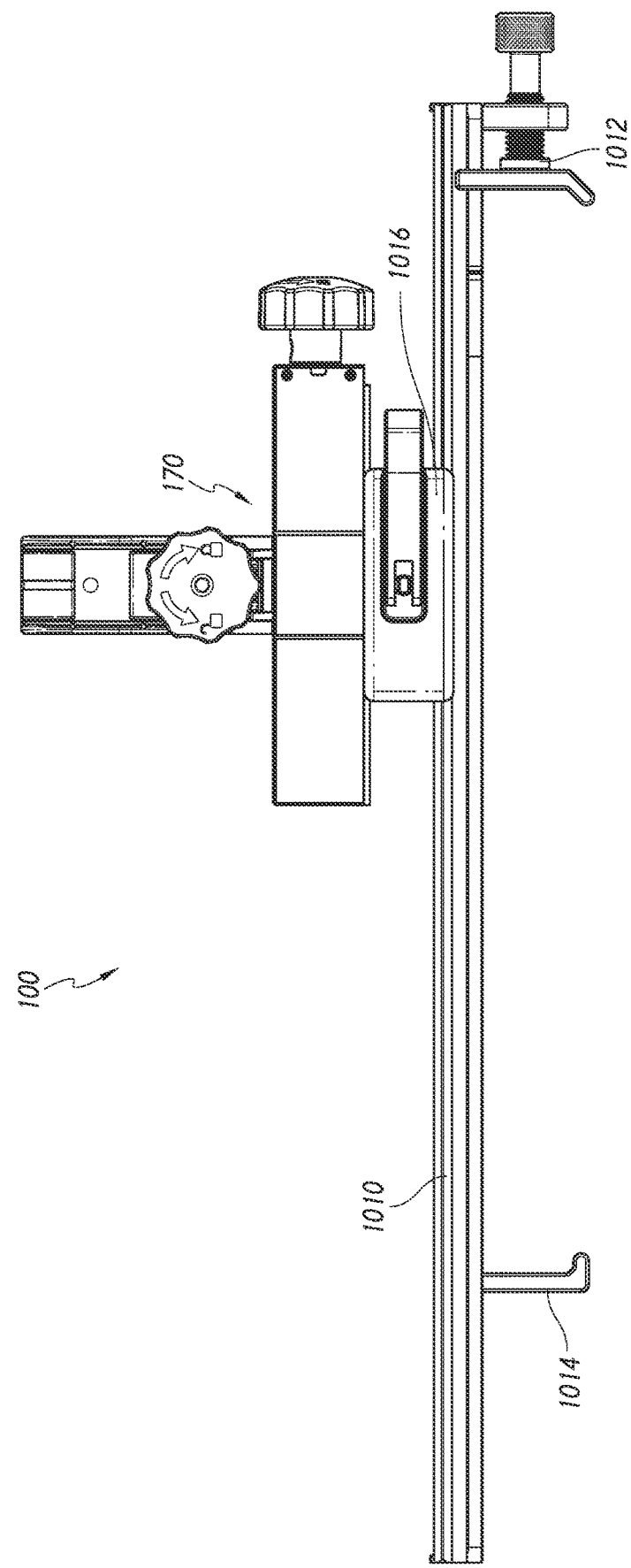
FIG. 19 illustrates an embodiment of a universal rail system.
Figure 20B:
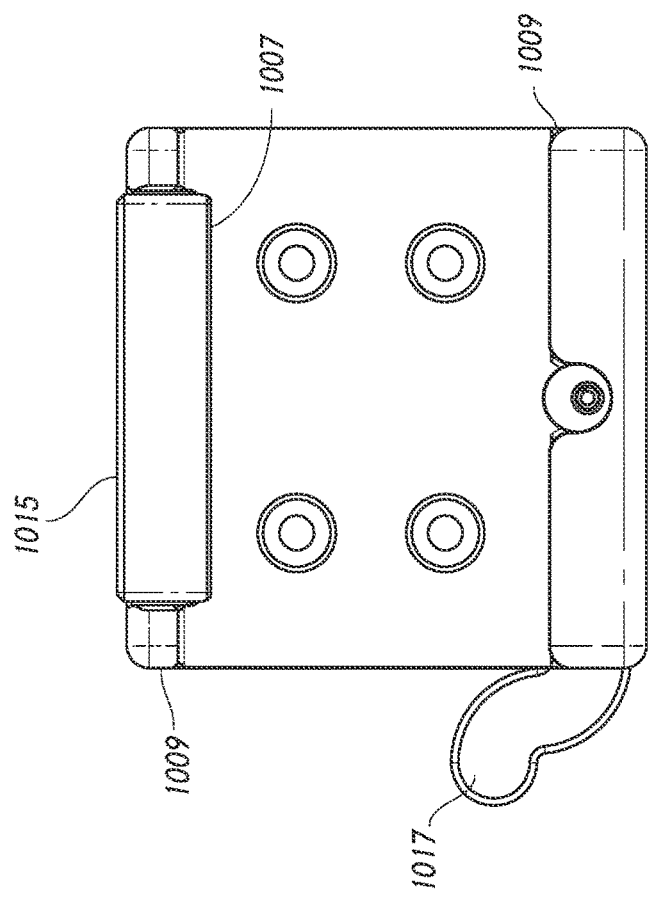
Figure 20A:
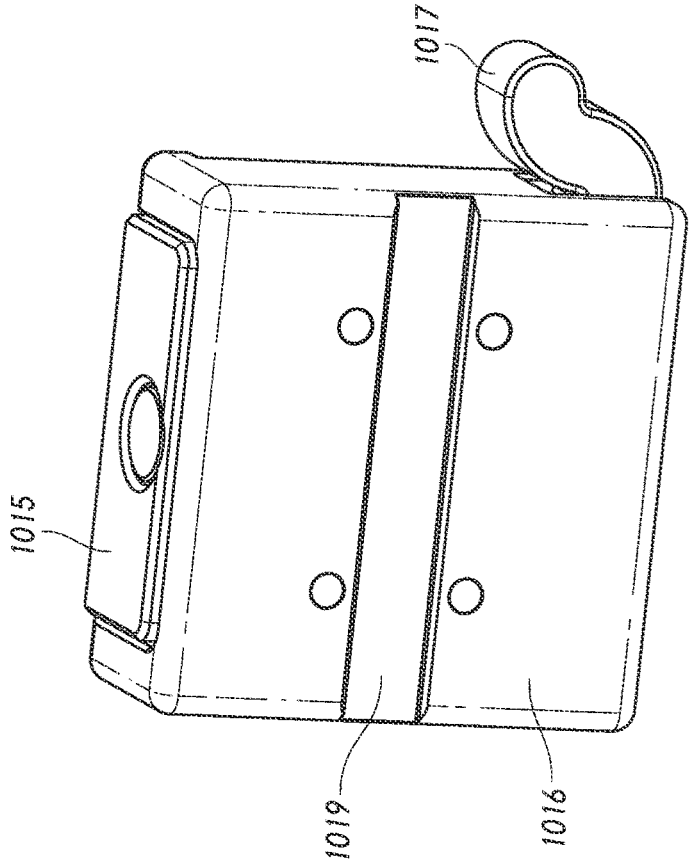
Figure 20E:
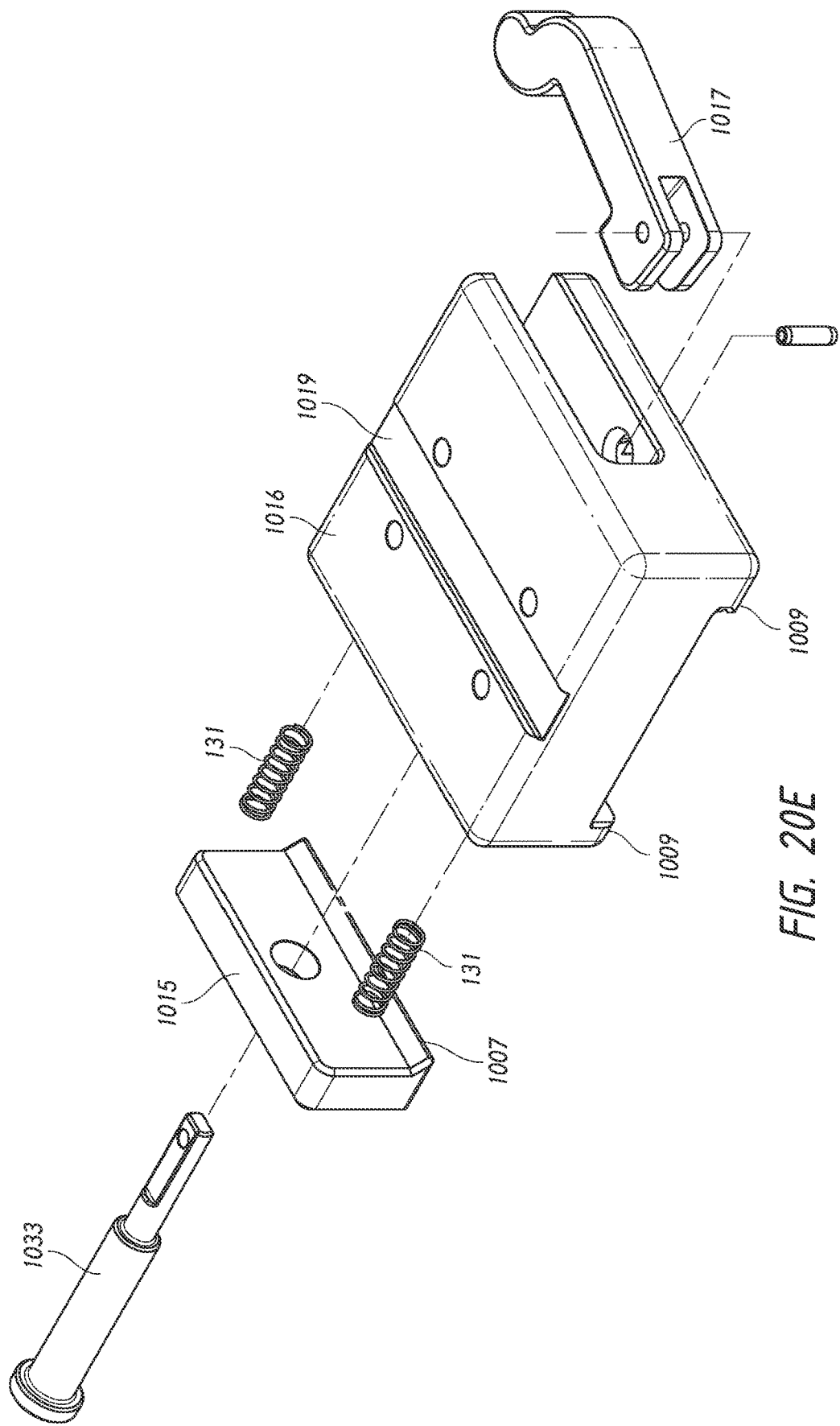
Figure 20F:
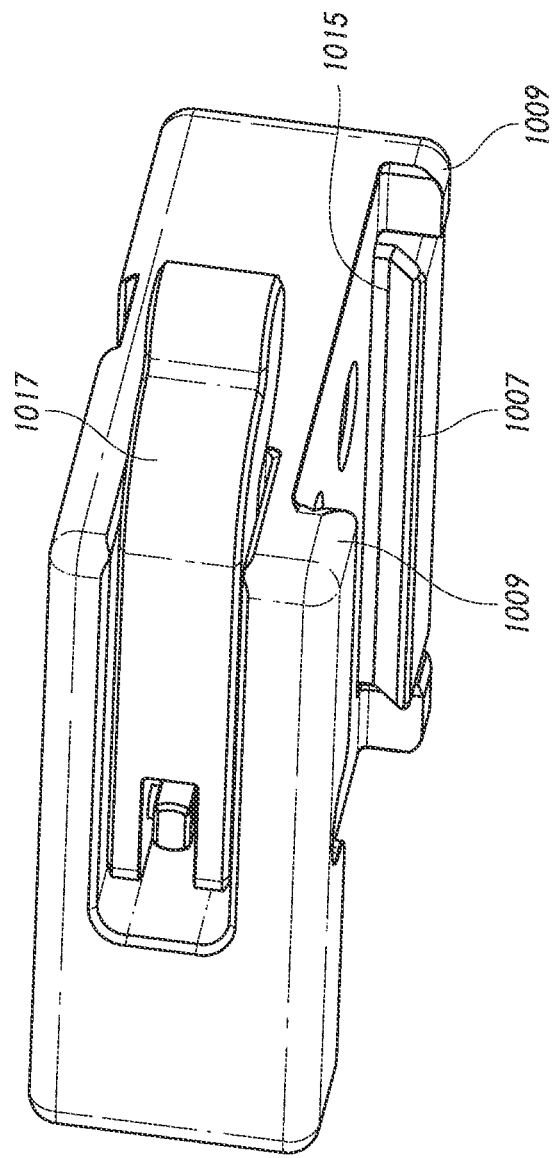

In some embodiments, the above described stabilizer 100 can utilize a universal stabilizer system 1000, such as shown in FIG. 19. Alternatively, only certain components from the above described stabilizer 100, such as guide assembly 170, may be used with the universal stabilizer. This system can be easily adaptable for different sized bases and delivery systems.

Similar to the above, a base 102 and a plate 104 can be used with a stabilizer 1000. However, the stabilizer 100 can utilize a universally attachable rail 1010 (instead of the clamps 120 and base plate 107), which may allow more flexibility and adaptability. However, these components may be used in the universal stabilizer system 1000 in some embodiments. In some embodiments, the base plate 207 may be attached directly to the rail 1010. In some embodiments, only the guide assembly 170 may be attached to rail 1010. In some embodiments, the guide assembly 170 and the hub nest 160 may be attached to rail 1010.

FIG. 19 illustrates an embodiment of the stabilizer 1000. As shown, the stabilizer 1000 can include a rail 1010, which may include moveable clamp 1012 and a stationary clamp 1014 spaced longitudinally apart. In some embodiments, both clamps may be moveable. As discussed in detail below, the moveable clamp 1012 can slide along the rail and be locked at a desired position on the rail, thus allowing the rail 1010 to be attached to different sized surfaces.

The stabilizer 1000 can further include a rail dock 1016, which can be used to attach a delivery system holder to the rail 1010. In some embodiments, the rail dock 1016 can be integrally formed with a delivery system holder. For example, the guide assembly 170 may be attached to an upper surface of the rail dock 1016. Different clamps on the delivery system holder can be used for different devices, and different delivery system holders can be swapped out and attached to the rail dock 1016 as needed. In some embodiments, multiple rail docks 1016 may be used along the rail 1010, for example holding both the guide assembly 170 in a proximal position and the hub nest 160 at a distal position. The rail dock 1016 may include similar angled surfaces as discussed above with respect to 130 and 150. In some embodiments, the rail dock 1016 can have an adjustable upper surface for adjusting angles.

As shown in FIGS. 20A-20F, the rail dock 1016 may have a bottom surface with protrusions 1009 that at least partially wraps around a top surface of the rail 1010 for allowing the rail dock 1016 to slide along the rail 1010, while preventing removal. The rail dock 1016 can further include a lock, such as a quick quarter lock, for attachment and detachment to the rail 1010 and for maintaining the position of the rail dock 1016 on the rail. As shown, the lock can include a handle 1017 rotatably connected to one side of the rail dock 1016 and attached, such as by a spring or pair of springs 1031 and a bolt or other attachment member 1033, to plate 1015 on an opposite side of the rail dock 1016. The handle 1017 can fit within a cutout on a side of the rail dock 1016 in some embodiments. Alternatively, buttons, knobs, or other actuators could be used in some embodiments. The handle 1017 can be rotated between a locked (FIG. 20C) and unlocked (FIG. 20D) position. By rotating the handle 1017 into the locked position, plate 1015 is compressed on the opposite side of the rail dock 1016 onto the rail 1010, such as through compression of the springs shown in FIG. 20E, which locks foot 1007 of plate 1015. This prevents motion of the rail dock 1016 and further prevents removal of the rail dock 1016 from the rail 1010. In the unlocked position, the rail dock 1016 can be slid off longitudinal ends of the rail 1010, or may be rotated towards the handle 1017 for removal, following a standard picatinny design. In some embodiments, the rail dock 1016, in either the locked or unlocked position, may not be lifted straight off the rail 1010. In some embodiments, the rail dock 1016 may include a Delrin base and PEEK handle 1017/plate 1016, though the type of material is not limiting. In some embodiments, the rail dock 1016 may be stationary on the rail 1010 and thus may not use a locking system.

FIG. 19 illustrates the guide assembly 170 attached ton upper surface of the rail dock 1016. As shown in FIGS. 20A-20F, in a configuration that is similar to second angled section 150, the rail dock 1016 may include a groove/slot 1019 on the upper surface in order to attach to a protrusion on the bottom surface of the guide assembly 170. Further attachment, such as screws, bolts, or magnets, can be used to more securely attach the guide assembly 170 to the rail dock 1016. However, the upper surface of the rail dock 1016 may be modified, and in some embodiments may not include the slot, may include any number of screw/bolt holes (1, 2, 3, 4, 5, 6), or other adjustments for attaching to different clamps.

Advantageously, the base 102 and plate 104 may be reusable and non-sterile, though remaining under a sterile field. The rail 1010 and the stationary clamp 1014 can both be reusable and sterile. In some embodiments, the moveable clamp 1012 and the rail dock 1016 may also be reusable and sterile. In alternative embodiments, one or both of the moveable clamp 1012 and the rail dock 1016 may be disposable and replaceable on the rail 1010. This can allow for modifications to the rail 1010 for adapting to different delivery devices and attachments.

Figure 21A:
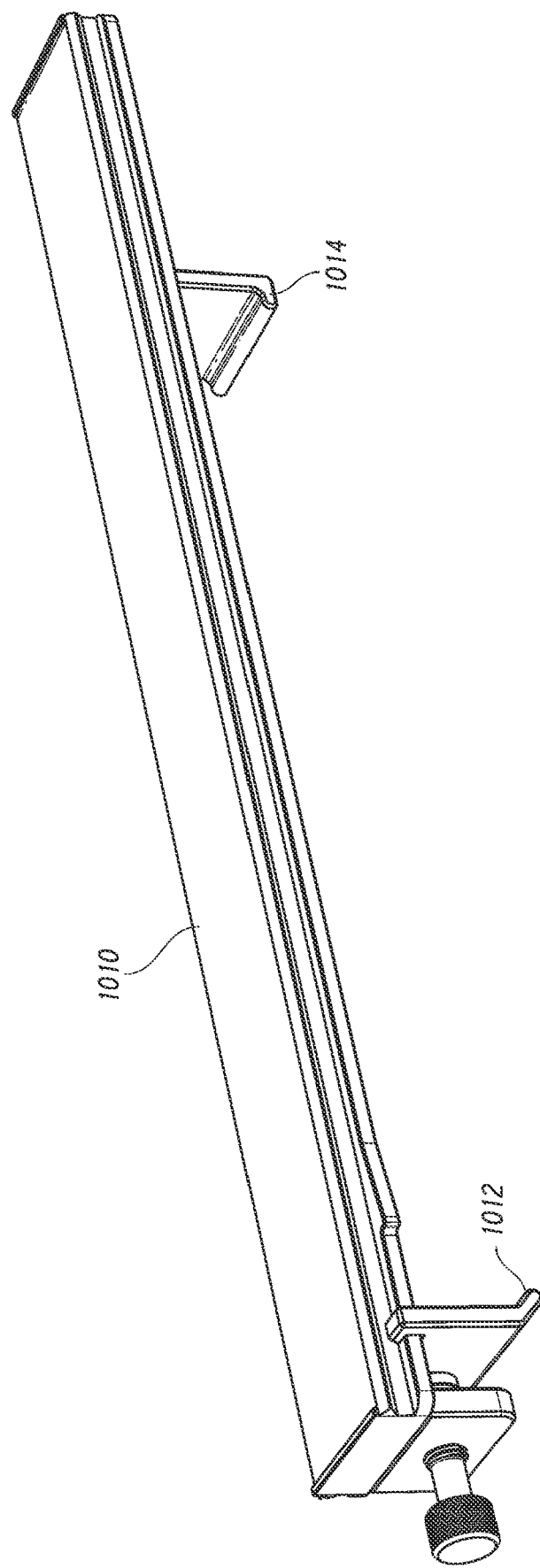
FIGS. 21A-21C illustrate embodiments of a rail.
Figure 21B:
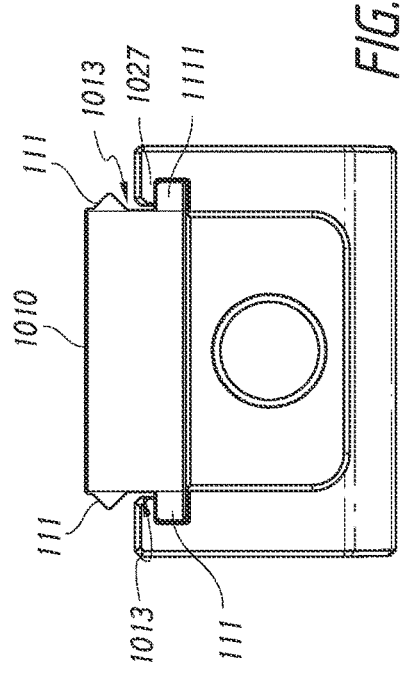
Figure 21C:
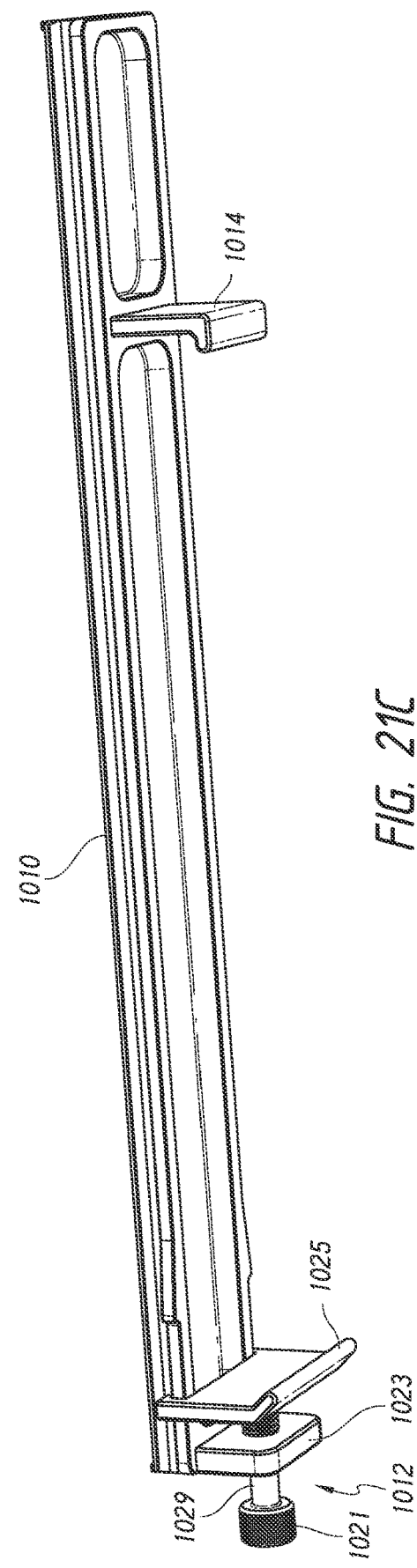

FIGS. 21A-21C show an embodiment of the rail 1010, which can be formed of metal, such as stainless steel, although the specific material is not limiting. In some embodiments, the rail 1010 is formed from a material that can be designed for reuse cleaning/autoclaving. A shown in FIG. 21B, which views the rail 1010 along a longitudinal line, the rail 1010 can include pairs of side protrusions 1111 extending outwardly away from the rail on each side orthogonal to the longitudinal axis, thereby forming a cavity 1013 between side protrusions 1111 on each side of the rail 1010. The protrusions 1111 can be rectangular or triangular, and the specific shape is not limiting. In some embodiments, the upper protrusion 1111 can be triangular and the lower protrusion 1111 can be rectangular. In some embodiments, protrusions 1111 on opposite sides may be differently shaped, or may be the same. Protrusions 1111 on the same side may be differently shaped or may be the same. Thus, inward extending arms of, for example, the rail dock 1016 or the moveable clamp 1012 can be held within the cavity 1013 to prevent release from the rail 1010. The protrusions 1111 can extend fully along the length of the rail 1010. In other embodiments, the protrusions 1111 may extend at least 90, 95, or 99% along the length of the rail 1010.

Figure 22B:
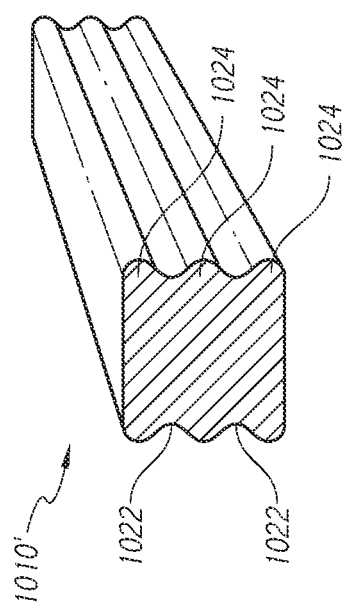
FIGS. 22A-22B illustrate embodiments of alternative rail cross-sections.
Figure 22A:
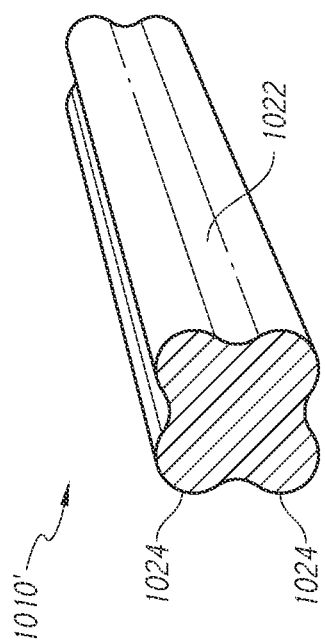

FIGS. 22A-22B illustrate alternate example embodiments of cross sections of the rail 1010. However, the cross sections are not intended to limit the shape and any type of cross-section can be used (such as rectangular cross sections). The rails 1010'/1010" can include divots 1022 and extensions 1024 (which may act like protrusions 1111 and cavity 1013).

Figure 24A:
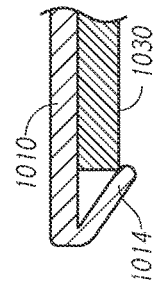
FIGS. 24A-24C illustrate embodiments of a stationary clamp attaching to different surfaces.
Figure 23:
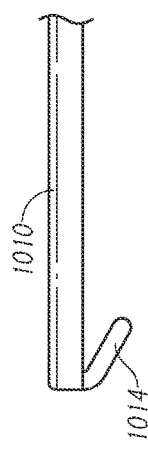
FIG. 23 illustrates an embodiment of a rail and stationary clamp.
Figure 24B:
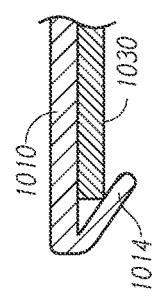
Figure 24C:
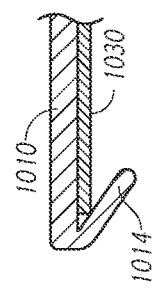

FIG. 23 illustrates a perspective of the rail 1010 and stationary clamp 1014. As shown, the stationary clamp 1014 can be integrated with the rail 1010, though in other embodiments it may be usable. The stationary clamp 1014 may be angled, and may be a hook, clamp, or other attachment mechanism. The stationary clamp 1014 may be flexible to allow for attachment to different thicknesses of surfaces 1030, such as shown in FIGS. 24A-24C. As shown in FIG. 21C, the stationary clamp 1014 may be inserted into a slot in the bottom surface of the rail 1010. The stationary clamp 1014 may be integrally formed with the rail 1010, mechanically, or chemically adhered.

FIG. 21C illustrates a view of an embodiment of the moveable clamp 1012. As discussed, the moveable clamp 1012 may be disposable or reusable. The clamp 1012 can be attached generally at one longitudinal end of the rail 1012.

The movable clamp 1012 can be formed from a knob 1021, an attached plate 1023 and a clamp 1025. The attached plate 1023 may be inserted into a slot in the bottom surface of the rail 1010. The attached plate 1023 may be integrally formed with the rail 1010, mechanically, or chemically adhered. The attached plate can hold a screw/bolt 1029 extending from knob 1021, such as through an aperture in the attached plate 1023. The end of the screw/bolt 1029 opposite the knob 1021 can mate with the clamp 1012. The clamp 1012 can includes protrusions 1027 (seen in FIG. 21B) on the upper surface to fit within the cavity 1013 on each side of the side of the rail 1010, thus allowing the clamp 1012 to slide along the rail 1010 while remaining attached. When the knob 1021 is turned, the clamp 1012 can move longitudinally along the rail 1010. This allows the clamp 1012 to compress onto different sized surfaces, allowing for the universal nature of the system 1000.

Figure 25:
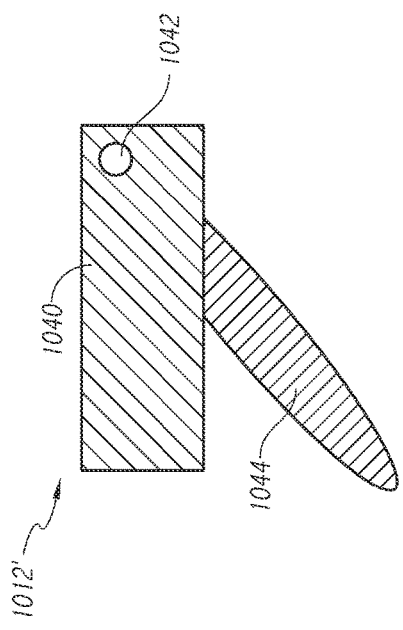
FIG. 25 illustrates an embodiment of a moveable clamp.

FIG. 25 shows an alternate embodiment of the moveable clamp 1012 as clamp 1012', and thus may incorporate some or all of the features discussed above with respect to moveable clamp 1012. As discussed, the moveable clamp 1012' may be disposable or reusable. As shown, the clamp 1012' may generally include a body 1040, a release 1042, and a clamp 1044. The body 1040 can interact with (e.g., attach to, couple with) the rail 1010. The body 1040 can slide along the rail 1010, such as within the cavities 1013. Further, the body 1040 can include a mechanism that prevents backward motion of the body 1040, thus preventing accidental release. The body 1040 can further contain a release actuator (knob, button, switch, etc.) that can be actuated to release the one-way mechanism, thus allowing the body 1040 to be moved away from the stationary clamp 1014. Further, the moveable clamp 1012' may include a clamp mechanism 1044 as discussed above with regards to the stationary clamp 1014. The clamp mechanism 1044 may be the same or different than the stationary clamp 1014.

As shown in FIGS. 26A-26B, the moveable clamp 1012 may be moved in order to easily and quickly clamp onto a surface 1030. In some embodiments, the moveable clamp 1012 can slide along an outer surface of the rail 1010. In some embodiments, the rail 1010 may contain an inner lumen, and the moveable clamp 1012 may contain a portion that slides within the inner lumen. In some embodiments, the moveable clamp 1012 may include a one-way sliding mechanism with a release, to allow for moving and locking of the moveable clamp 1012.

FIG. 27 illustrates an embodiment of the rail 1010 with the clamps 1012/1014/1016 removed. As shown, the rail 1010 can include wings or feet 1018. These wings 1018 may be integrated with the rail 1010, or removable and attachable. The wings 1018 may provide additional support and stability, to prevent any rocking of the rail 1010. Thus, the wings 1018 may contact a surface the rail 1010 is on while the system is in use. As shown, the wings 1018 may be located near the stationary clamp 1014, though the position of the wings 1018 is not limiting.

Figure 28:
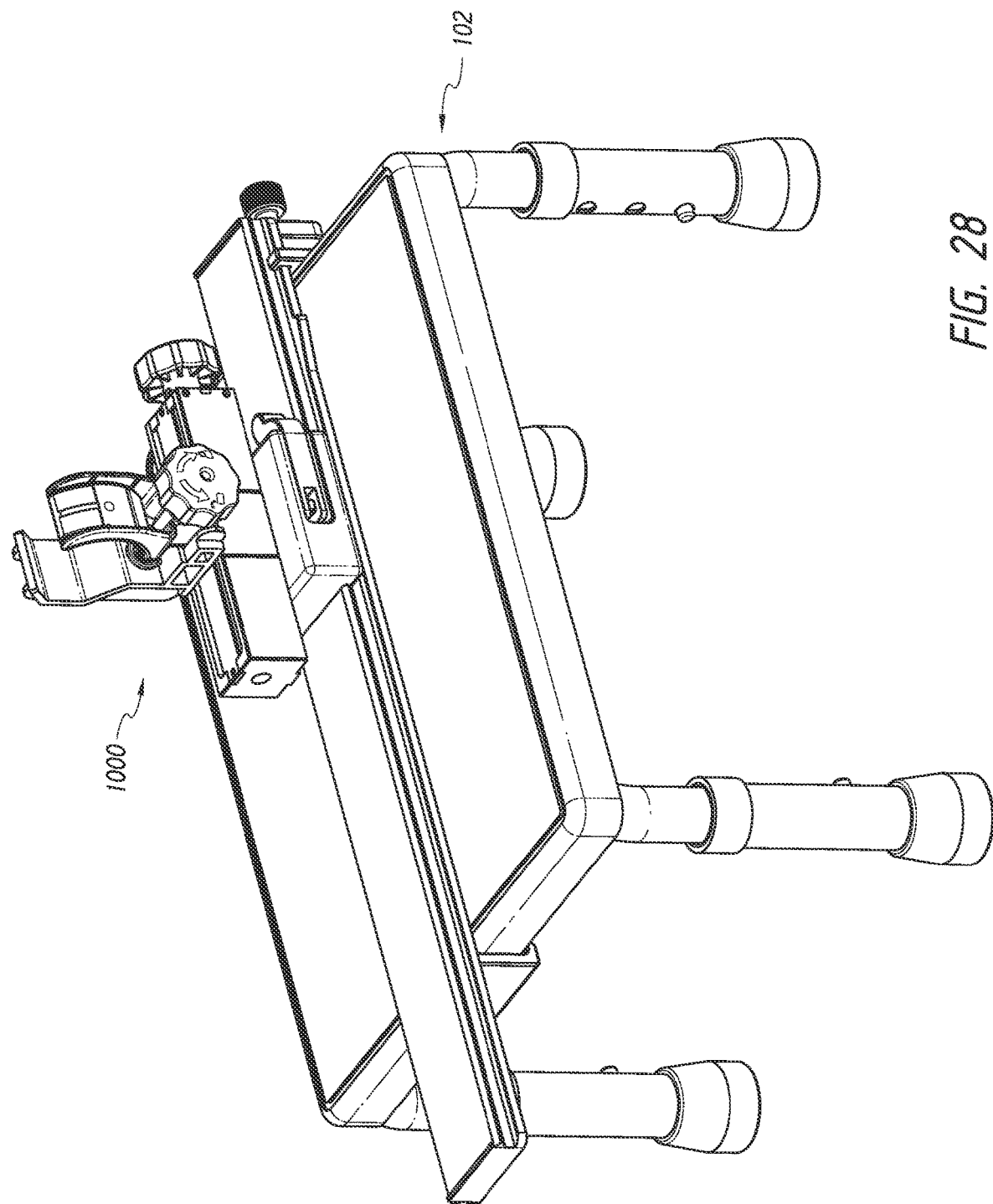
FIG. 28 illustrates an embodiment of a universal rail system.

FIG. 28 illustrates an embodiment of the above disclosed system 1000 on base 102.

Electronic and Motorized Control

In some embodiments, the stabilizer 100 (or stabilizer 1000) can be electronically controlled. Thus, a user does not need to directly interact with the stabilizer 100/1000 once a delivery system is installed and the stabilizer 100/1000 is attached to a surface in order to move the delivery system. For example, any of the knobs (127, 178, 183, 1021) or other actuators on the stabilizer 100/1000 can be electronically controlled, such as through a computer, phone application, controller (wireless or directly connected), or other operation. In some embodiments, the position of the rail dock 1016 can be electronically controlled as well. Thus, in some embodiments the stabilizer 100/1000 may include a motor to manipulate the actuators on the stabilizer 100/1000. Further, the stabilizer 100/1000 could include motors/sensors/controls to operate the delivery system remotely. This can provide an option for a semi-robotic procedure wherein the stabilizer's primary function is more akin to an actuation tool. Because the stabilizer is capable of actuating knobs, a physician could implant a valve via a remote location. Alternatively, if the physician was in a location with the stabilizer 100/1000, the electronic control can assist the physician and/or allow the physician to spend more time looking at the visualization.

As an example, a controller could operate knob 178 in order to move handle carriage 180 along the screw 176 in either stabilizer 100/1000, thus providing distal and proximal motion of the delivery system. The controller could include locking features to prevent inadvertent motion.

In some embodiments, feedback from visualizations (x-ray, fluoroscopy, etc.) can be used to improve delivery and reduce the chance of vascular damage. For example, the stabilizer 100/1000 could stop any movement automatically to avoid contacting/damaging a patient's anatomy. In some embodiments, sensors and/or visualization could be included to measure and provide feedback, such as deflection angle of the delivery system. Sensors can be incorporated into the delivery system, and could be in communication with, such as wirelessly, with the stabilizer 100/1000. The sensors could be used to detect parameters including, but not limited to, force, pressure, position, deflection, or rotation. An electronically controlled system may also utilize artificial intelligence, such as using machine learning, to enhance the procedure. Data from previous procedures, especially from patients with similar anatomies, could be utilized to help direct the advancement of the catheter and deployment of the prosthetic valve. In an advanced embodiment, the entire procedure could be performed autonomously with near perfect accuracy by utilizing large amounts of data and experience from previously performed procedures.

Figures 29, 30:
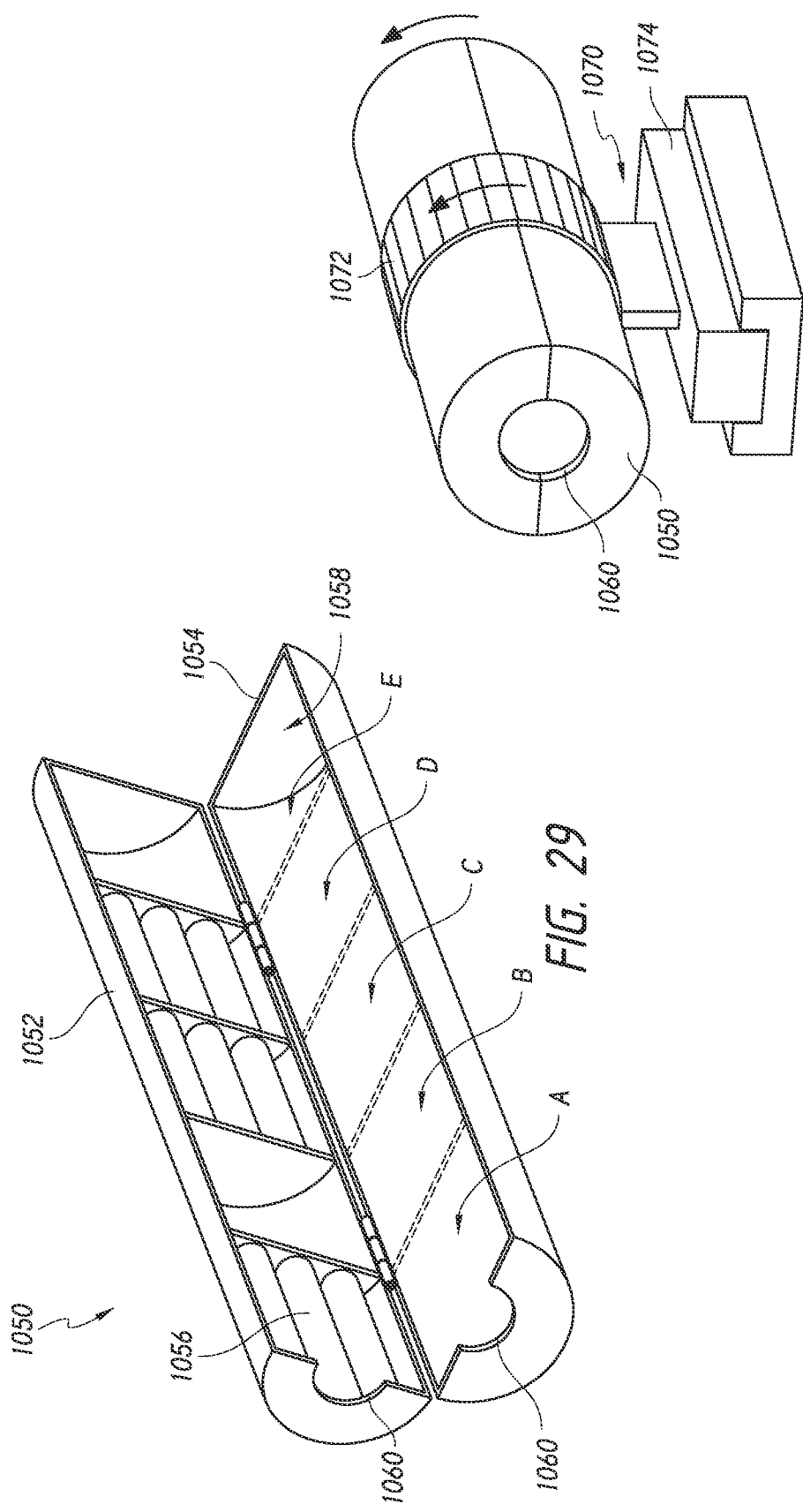
FIG. 29 illustrates a motorized knob delivery system rotation mechanism.
FIG. 30 illustrates a motorized delivery system rotation mechanism.

FIGS. 29 and 30 illustrate embodiments of motorized controls. These controls can utilize any of the above electronic/motorized controls and can be incorporated into any of the disclosed stabilizers and delivery systems. Alternatively, they can be used separately.

FIG. 29 illustrates an embodiment of a knob control system 1050. The system 1050 can be designed to fit around a portion, or all, of a handle of a delivery system (such as delivery system 300). FIG. 29 illustrates a clamshell design formed from an upper half 1052 and a lower half 1054, which can form a holder/container. The handle can fit within a cavity 1058 in the lower half 1054, and any shafts can extend out an aperture 160 in the system 150. The upper half 1052 may contain rollers 1056, such as compression rollers, which can apply friction to any knobs on the delivery system once the system 1050 is closed around a handle. The lower half 1054 may also contain rollers 1056, either along with the upper half 1052 or instead of the upper half 1052 having rollers 1056. While a clamshell is an example design, other designs can be used that can partially or fully contain a delivery system handle. Further, other mechanisms for actuating knobs on the delivery system can be used as well instead of or in conjunction with the rollers.

The system 1050 can include a variety of different sections A-E along a length of the system 1050. The number of sections is not limiting, and can include 1, 2, 3, 4, 5, 6, 7, 8, 9, or 10 sections. The sections may be physically isolated from one another, such as by a barrier or wall, or may just be separate connected areas with different components. All or some of the sections may include rotatable components, such as rollers 1056, or may themselves rotate. The number of rotatable sections may be the same as the number of rotatable knobs on a delivery system. For example, 1, 2, 3, 4, 5, 6, 7, 8, 9, or 10 sections may include rotatable components. By rotating the rollers 1056 in a rotatable section which are frictionally pressed against a knob on a handle, they would rotate their respective knob/actuator on the delivery system. Thus, by individually rotating the rollers 1056 in different sections, different knobs can be actuated on the handle. The rollers 1056 in different sections can apply different forces on the handle. Some sections may not include rotatable components and may be a tighter fit to hold the handle in place while other sections are rotating, thereby allowing the knobs to be actuated. The rotatable sections may be rotated individually or may be rotated together as desired by a user.

The system 1050 can be attached to a motor (or may contain a motor within or outside the system 1050) in order to rotate the components in different rotatable sections. In some embodiments, the motor can be an encoder, which can track the number of rotations and location of each section. The motor can be operated wired or wirelessly, as discussed above.

FIG. 30 illustrates an embodiment of a motorized control system 1070 for manipulating a handle of a delivery system. Unlike system 1050, system 1070 is used to move the handle as an entire unit. In some embodiments, system 1070 may not be used and system 1050 may be configured to fully rotate the handle as well as the different knobs. The system 1070 can include a rotatable band/strap/holder 1072 that can wrap around a handle of a delivery system or may wrap around a stationary section of system 1050. The band 1072 may frictionally hold the handle or system 1050 or may be mechanically or chemically adhered. The band 1072 can be rotated to fully rotate the delivery system. Further, the system 1070 may include a stand/base 1074. The base 1074 may be located on track 1076 or other translatable component. The base 1074 can be translated along the track 1076 to provide axial/longitudinal motion to the delivery system. Both the track 1076 and band 1072 may be operated by a motor, such as discussed herein. The same motor can be used to operate systems 1070 and 1050. In some embodiments, different motors are used.

Thus, if both system 1070 and 1050 are used at the same time, a user can individually manipulate different knobs as well as translate the delivery system rotationally or axially. The different moveable components discussed herein can all be operated electronically.

Magnetic Attachment

As discussed above, the stabilizer 100/1000 utilizes atraumatic clamps (120, 1012, 1014) to attach the stabilizer 100/1000 to the base 102. The base 102 is typically under a sterile drape and the stabilizer 100/1000 is on top of the drape, and therefore the connection between the two is such that the sterile field is maintained. Preferably, the connection is robust, but also quick so as not to delay the procedure, while also being atraumatic to the sterile drape. Further, it can be useful for the connection to be able to be removed quickly if the stabilizer 100/1000 needs to be moved and the delivery system handle 300 handled manually. While the above discussed clamps can achieve all these advantages, other attachment/connections can be utilized instead of or in conjunction with the clamps. Thus, magnetic attachment could replace any and all the above disclosed clamps. In some embodiments, the base adapter 140 may be removed with the use of the magnetic attachment. Further, the flange 204 may be removed from the base plate 207 so that the stabilizer 100/1000 has a flat bottom surface. For stabilizer 1000, clamps 1012 and 1014 could be removed.

In some embodiments, a magnet (such as a magnetic clamping mechanism, magnetic clamp, etc.) can be used to attach the stabilizer 100/1000 to the base 102. The magnetic clamp could be removed easily, and would be a quick, reliable, method for attaching the stabilizer 100/1000 to the base 102. In some embodiments, the stabilizer 100/1000 is brought into place after the delivery system has already crossed into the native mitral valve, and thus connection speed can be a useful feature. By using a magnetic system, the stabilizer 100/1000 can be attached quickly and would be secured until the end of the procedure.

In some embodiments, the base 102 can be made of a magnetic material in which the stabilizer 100/1000, which can be at least partially a metal, can easily adhere to. For example, the upper surface 106 of the base 102 can be formed of a magnetic material. In some embodiments, the whole upper surface 106 can be formed of a magnetic material. In some embodiments, the upper surface 106 may include a strip of magnetic material. This strip may have dimensions equivalent to, greater than, or smaller than that of the footprint of the stabilizer 100/1000. In some embodiments, magnetic material may be attached to an upper surface of the upper surface 106, which can then be covered by the sterile drape. As the base 102 is under the drape away from magnetically sensitive equipment, it can be an advantageous area to place the magnetic feature.

In some embodiments, a magnet can be attached to a bottom surface of the stabilizer 100/1000, such as on a bottom surface of the base plate 207 or rail 1010. In some embodiments, a portion or an entirety of the base plate 207 or rail 1010 can be made of a magnetic material. The base 102 can then be made of metal, or other material that is magnetically attracted to the magnet.

In some embodiment, the magnetic features disclosed above can be an electromagnet or dipole system. Thus, a user can turn the magnetic field on or off, such as through a button, switch, controller, computer, app, etc. Thus, the magnetic connection could be made even stronger and when the procedure was complete, an operator can turn off the magnetic field and remove the stabilizer 100/1000 with ease.

From the foregoing description, it will be appreciated that inventive stabilizers are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method of using a stabilizer to assist with implantation of a replacement heart valve, comprising:
   inserting a portion of a heart valve delivery system having the replacement heart valve through vasculature of a patient to a native heart valve within a heart of the patient,
   wherein the heart valve delivery system includes a handle comprising actuators;
   clamping a base adapter to a base or table;
   locating the base or table over the patient;
   inserting a distal portion of a main body of the stabilizer into the base adapter;
   clamping a proximal end of the main body of the stabilizer to the base or table;
   attaching the heart valve delivery system to the main body of the stabilizer by placing a portion of the handle without any actuators into a C-shaped clamp of a handle carriage forming part of the main body of the stabilizer, the clamp comprising a stationary first clamp half and an adjustable second clamp half, wherein the second clamp half is configured to be moved toward and away from the first clamp half to controllably tighten or loosen the clamp around the handle; and
   adjusting a position of the handle carriage longitudinally along the base or table by turning a knob affixed to a travel screw,
   wherein the handle carriage further comprises spring plungers which mate with detents on the knob to provide tactile feedback.

2. The method of claim 1, wherein attaching the heart valve delivery system to the main body comprises sliding a distal end of the heart valve delivery system through a sheath hub.

3. The method of claim 2, wherein the sheath hub is attached to a hub nest of the stabilizer after sliding the distal end of the heart valve delivery system through the sheath hub.

4. The method of claim 2, wherein the sheath hub is attached to a hub nest prior to sliding the distal end of the heart valve delivery system through the sheath hub.

5. The method of claim 2, wherein the sheath hub is configured to rotate within a hub nest.

6. The method of claim 2, further comprising adjusting a position and angle of a hub nest adapter.

7. The method of claim 1, wherein the second clamp half is configured to be moved toward and away from the first clamp half to controllably tighten or loosen the clamp around the handle by turning a knob that is operably coupled to a screw or bolt connected to the first clamp half and the second clamp half.

8. The method of claim 1, wherein the handle carriage is movably attached to a housing.

9. The method of claim 8, wherein the handle carriage is adapted to move up to 130 mm.

10. The method of claim 1, wherein adjusting the position of the handle carriage longitudinally along the base or table comprises advancing or retracting the distal end of the heart valve delivery system axially with respect to the native heart valve.

11. The method of claim 10, further comprising delivering the replacement heart valve at the location of the native heart valve of the patient using the heart valve delivery system.

12. The method of claim 11, further comprising removing the heart valve delivery system from the patient and from the stabilizer after delivering the replacement heart valve at the location of the native heart valve of the patient.

13. The method of claim 1, further comprising aligning the patient substantially perpendicular to the stabilizer.

14. The method of claim 1, further comprising aligning the patient substantially parallel to the stabilizer.

15. The method of claim 1, wherein the native heart valve is a tricuspid valve.

16. A method of using a stabilizer to assist with implantation of a replacement heart valve, comprising:

inserting a portion of a heart valve delivery system having the replacement heart valve through vasculature of a patient to a native heart valve within a heart of the patient, wherein the heart valve delivery system includes a handle;

clamping a base adapter to a base or table;

locating the base or table over the patient;

inserting a distal portion of a main body of the stabilizer into the base adapter;

clamping a proximal end of the main body of the stabilizer to the base or table;

attaching the heart valve delivery system to the main body of the stabilizer by placing a portion of the handle into a clamp of a handle carriage forming part of the main body of the stabilizer; and adjusting a position of the handle carriage longitudinally along the base or table by turning a knob affixed to a travel screw, wherein the handle carriage further comprises detents on the knob to provide tactile feedback.

17. The method of claim 16, wherein attaching the heart valve delivery system to the main body of the stabilizer comprises sliding a distal end of the heart valve delivery system through a sheath hub.

18. The method of claim 16, wherein adjusting the position of the handle carriage longitudinally along the base or table causes advancement or retraction of the distal end of the heart valve delivery system axially with respect to the native heart valve.

19. The method of claim 16, wherein adjusting the position of the handle carriage longitudinally along the base or table is controlled using spring plungers which mate with the detents on the knob.

20. The method of claim 16, wherein the native heart valve is a tricuspid valve.

* * * * *